(12) United States Patent
Stevens et al.

US011176326B2

(10) Patent No.: US 11,176,326 B2
(45) Date of Patent: Nov. 16, 2021

(54) COGNITIVE ANALYSIS OF CRITERIA WHEN INGESTING DATA TO BUILD A KNOWLEDGE GRAPH

(71) Applicant: International Business Machines Corporation, Armonk, NY (US)

(72) Inventors: Richard J Stevens, Monkton, VT (US); Fernando Jose Suarez Saiz, Armonk, NY (US); Eric W. Will, Rochester, MN (US); Adam Clark, Mantorville, MN (US)

(73) Assignee: International Business Machines Corporation, Armonk, NY (US)

( * ) Notice: Subject to any disclaimer, the term of this patent is extended or adjusted under 35 U.S.C. 154(b) by 169 days.

(21) Appl. No.: 16/238,675

(22) Filed: Jan. 3, 2019

(65) Prior Publication Data
US 2020/0218779 A1    Jul. 9, 2020

(51) Int. Cl.
*G06F 40/30* (2020.01)
*G06N 5/04* (2006.01)
(Continued)

(52) U.S. Cl.
CPC ............ *G06F 40/30* (2020.01); *G06N 5/048* (2013.01); *G06Q 10/04* (2013.01); *G06Q 10/06316* (2013.01)

(58) Field of Classification Search
CPC .. G06Q 10/04; G06Q 10/06316; G06F 40/30; G06N 5/048
See application file for complete search history.

(56) References Cited

U.S. PATENT DOCUMENTS 8,793,145 B2    7/2014  Kahn et al.
2016/0117470 A1*  4/2016  Welsh .................... G16H 50/70
                                                        705/3
(Continued)

FOREIGN PATENT DOCUMENTS

WO    2018077906    5/2018

OTHER PUBLICATIONS

Kopcke, Felix, et al., "Evaluating Predictive Modeling Algorithms to Assess Patient Eligibility for Clinical Trials from Routine Data," BMC Medical Informatics and Decision Making 13, No. 1, 2013, 9 pages.

(Continued)

*Primary Examiner* — Thomas H Maung
(74) *Attorney, Agent, or Firm* — Patterson + Sheridan, LLP

(57) ABSTRACT

Techniques for cognitive analysis of documents are provided. A document corresponding to a clinical trial is received. Criteria are identified for the clinical trial based on processing the electronic document using natural language processing (NLP) techniques, where the criteria specify attributes of individuals that are eligible for the trial. Further, the criteria are analyzed using NLP techniques to determine a respective confidence level for each respective criterion, where the confidence level indicates a degree of certainty that the criterion is applicable to the trial. A knowledge graph is generated based at least in part on the clinical trial, where the confidence level assigned to each criterion is included in the knowledge graph for subsequent use. Finally, one or more therapies in the knowledge graph are selected to be recommended, based on a patient profile and the confidence level assigned to each of the criteria.

20 Claims, 12 Drawing Sheets

(51) Int. Cl.
  *G06Q 10/04* (2012.01)
  *G06Q 10/06* (2012.01)

(56) References Cited

U.S. PATENT DOCUMENTS

2016/0246945 A1* 8/2016 Allen ..................... G16H 20/40
2016/0306791 A1* 10/2016 Allen ................. G06F 16/3329

OTHER PUBLICATIONS

Lee, Yugyung, et al., "A Semantic Framework for Intelligent Matchmaking for Clinical Trial Eligibility Criteria," ACM Transactions on Intelligent Systems and Technology (TIST) 4, No. 4, 2013, 32 pages.
Krishnamoorthy, Saranya, "A Data Driven Semantic Framework for Clinical Trial Eligibility Criteria," PhD diss., University of Missouri-Kansas City, 2012, 108 pages.

* cited by examiner

COGNITIVE ANALYSIS OF CRITERIA WHEN INGESTING DATA TO BUILD A KNOWLEDGE GRAPH

BACKGROUND

The present disclosure relates to document analysis, and more specifically, to cognitively analyzing stated criteria when ingesting data to build a knowledge graph.

In a variety of domains, studies, experiments, and trials are performed to understand how potential options or selections interact and compare to each other. For example, in the medical field, studies and trials are performed to determine the efficacy of new and existing therapies, in order to determine the best practices for treating or curing illnesses or disorders. Frequently, the results of these studies, experiments, and trials are published for review by others. Currently, the published literature is reviewed manually by subject-matter experts (SMEs) to determine the state of the field, and provide guidance with respect to optimal therapies. However, these determinations are time-consuming, expensive, and inherently biased. Further, the published literature is expanding at an increasing and unprecedented rate. As the number of published documents increases, it has become impossible to aggregate and interpret them all. Thus, current guidelines and best practices are universally outdated, and potentially conflict with newly discovered therapies or interactions.

Additionally, when patients are to be treated, healthcare providers rely on the defined guidelines in order to determine which treatments or therapies are appropriate for a given patient. However, given the rapid pace and complexity of the published literature, as well as the enormous amount of data that must be considered, it is impossible for healthcare providers to identify and evaluate all of these potential therapies in view of their respective guidelines. Thus, patient outcomes are often worse than they could be. Typically, published literature indicates the applicability of the research (e.g., the patients to which the study applies) through specified criteria. However, these criteria are often incomplete, inaccurate, misleading, or ambiguous. This uncertainty can significantly impact the quality of decisions made based on the literature.

SUMMARY

According to one embodiment of the present disclosure, a method is provided. The method includes receiving a first electronic document corresponding to a first clinical trial, and identifying a first plurality of criteria for the first clinical trial based on processing the first electronic document using one or more natural language processing (NLP) techniques, wherein the first plurality of criteria specifies attributes of individuals that are eligible for the first clinical trial. The method further includes analyzing the first plurality of criteria using one or more NLP techniques to determine a respective confidence level for each respective criterion of the first plurality of criteria, wherein the respective confidence level indicates a degree of certainty that the respective criterion is applicable to the first clinical trial. Additionally, the method includes generating a knowledge graph based at least in part on the first clinical trial, wherein the confidence level assigned to each respective criterion is included in the knowledge graph for subsequent use. Finally, the method includes selecting one or more therapies in the knowledge graph to be recommended, based at least in part on a patient profile and the confidence level assigned to each of the first plurality of criteria.

According to a second embodiment of the present disclosure, a computer-readable storage medium is provided. The computer-readable storage medium has computer-readable program code embodied therewith, the computer-readable program code executable by one or more computer processors to perform an operation. The operation includes receiving a first electronic document corresponding to a first clinical trial, and identifying a first plurality of criteria for the first clinical trial based on processing the first electronic document using one or more natural language processing (NLP) techniques, wherein the first plurality of criteria specifies attributes of individuals that are eligible for the first clinical trial. The operation further includes analyzing the first plurality of criteria using one or more NLP techniques to determine a respective confidence level for each respective criterion of the first plurality of criteria, wherein the respective confidence level indicates a degree of certainty that the respective criterion is applicable to the first clinical trial. Additionally, the operation includes generating a knowledge graph based at least in part on the first clinical trial, wherein the confidence level assigned to each respective criterion is included in the knowledge graph for subsequent use. Finally, the operation includes selecting one or more therapies in the knowledge graph to be recommended, based at least in part on a patient profile and the confidence level assigned to each of the first plurality of criteria.

According to a third embodiment of the present disclosure, a system including one or more computer processors and a memory is provided. The memory contains a program which when executed by the one or more computer processors performs an operation. The operation includes receiving a first electronic document corresponding to a first clinical trial, and identifying a first plurality of criteria for the first clinical trial based on processing the first electronic document using one or more natural language processing (NLP) techniques, wherein the first plurality of criteria specifies attributes of individuals that are eligible for the first clinical trial. The operation further includes analyzing the first plurality of criteria using one or more NLP techniques to determine a respective confidence level for each respective criterion of the first plurality of criteria, wherein the respective confidence level indicates a degree of certainty that the respective criterion is applicable to the first clinical trial. Additionally, the operation includes generating a knowledge graph based at least in part on the first clinical trial, wherein the confidence level assigned to each respective criterion is included in the knowledge graph for subsequent use. Finally, the operation includes selecting one or more therapies in the knowledge graph to be recommended, based at least in part on a patient profile and the confidence level assigned to each of the first plurality of criteria.

DETAILED DESCRIPTION

Figure 1:
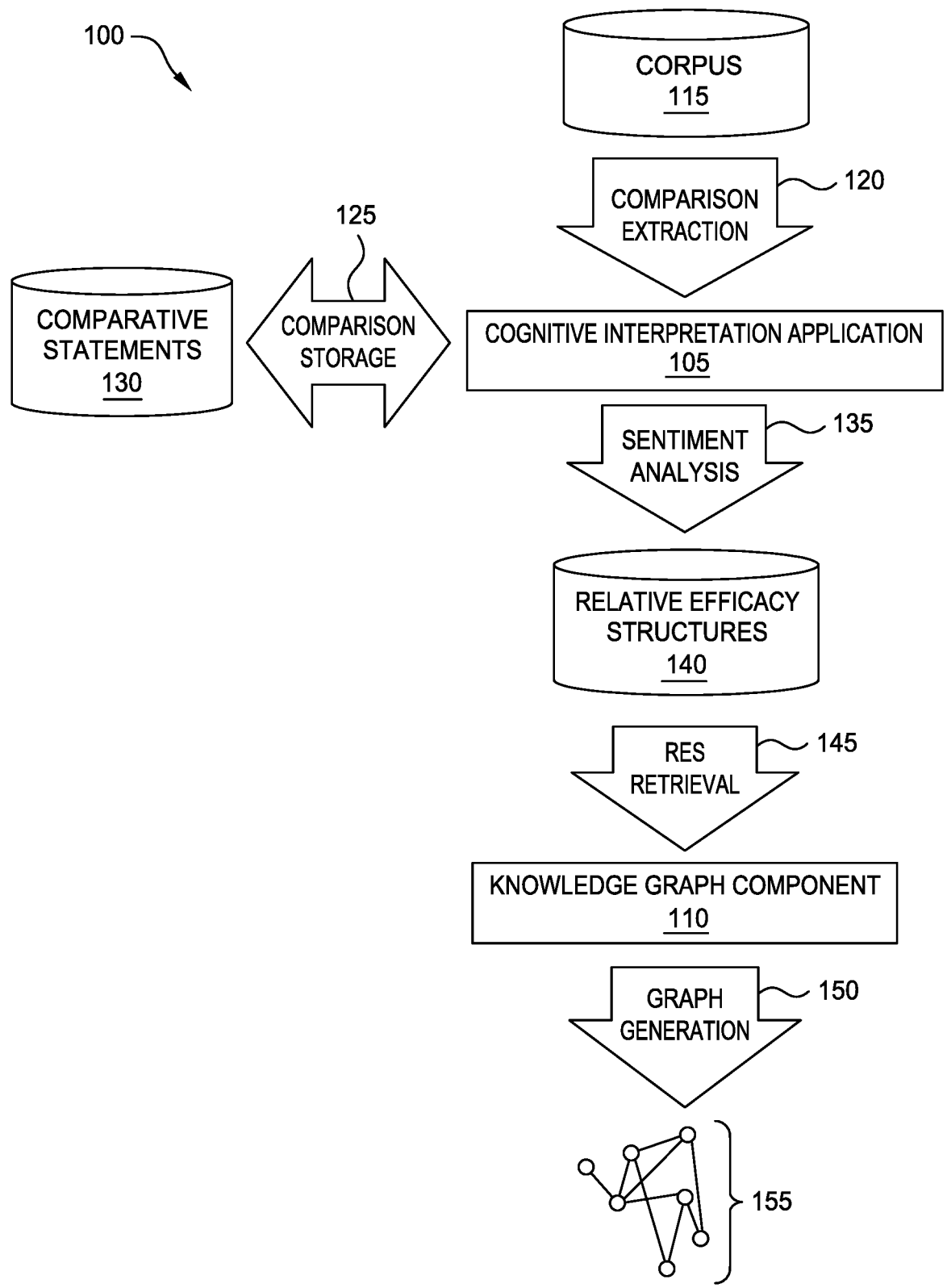
FIG. 1 illustrates a workflow for cognitively determining the relative efficacy of therapies, according to one embodiment disclosed herein.

In order to make informed decisions regarding treatment or therapy selections, healthcare providers rely on published literature establishing the efficacy and safety for a number of available therapies. In some embodiments of the present disclosure, the published literature is evaluated and analyzed to generate a knowledge graph representing the relationships and relative efficacies of any number of therapies. In an embodiment, in order to select a therapy for a particular patient, the knowledge graph is analyzed to identify literature that is relevant to the patient (e.g., based on the patient's attributes). In some embodiments, documents are weighted for the index patient based on how closely the patient's attributes align with the criteria specified in the document. However, if the document's specified criteria are inaccurate or ambiguous, a therapy may be erroneously suggested or recommended. Embodiments of the present disclosure enable cognitive and dynamic evaluation of specified criteria, in order to construct a knowledge graph that accounts for these uncertainties and ambiguities. In one embodiment, the literature can then be weighted based not only on the criteria specified, but also based on a confidence level for each criterion.

In one embodiment, a criteria evaluator parses each specified criterion using one or more natural language processing (NLP) techniques to identify internal ambiguity or contradiction. For example, suppose a criterion specifies that the results apply to patients who have a "BMI under thirty and age under 65 or are hypertensive." In an embodiment, the evaluator can determine that this criterion is ambiguous because it is not clear what the author intended. For example, one interpretation is that the results apply to those who have a BMI under thirty, who also are either under 65 or are hypertensive (e.g., the patient must have a BMI under thirty). Another interpretation is that the results apply to patients who have a BMI under thirty who are also under 65, or patients who are hypertensive (e.g., if the patient is hypertensive, BMI and age are irrelevant). In embodiments, the criteria evaluator can utilize predefined patterns to identify these internal ambiguities or contradictions. In some embodiments, the evaluator utilizes a machine learning (ML) model that has been trained with labeled exemplars to score the ambiguity or inconsistency for new criteria.

In some embodiments, the criteria are evaluated based on the title, description, or other text associated with the document. For example, if a criterion specifies that the results apply to patients who are younger than 65, but the title indicates that the study was performed to research the effect of a therapy on patients over 65, the evaluator can determine that this criterion is inconsistent with stated purpose of the document. This may be, for example, due to a typographical error. Further, in one embodiment, the criteria are evaluated based on the actual attributes of participants who enrolled or participated in the trial associated with the document. For example, suppose a criterion states individuals are not eligible for participation if they are younger than 25. If one or more of the actual participants are younger than 25, the evaluator can reduce confidence or weight associated with the criterion, because there is evidence it was not actually followed (or not strictly followed).

In one embodiment, the criteria are also evaluated based on other published literature. For example, in one embodiment, other similar documents are identified (e.g., studying the same or a similar therapy, or a similar disorder). The criteria specified by each of these documents can then be analyzed, and the criteria specified by the index document (e.g., the document being ingested) can be compared to the existing literature to determine whether it is cohesive or similar to the existing literature. For example, if 75% of the documents studying the use of a particular therapy to treat a particular disorder specify a first criteria, it is unsurprising that the index document also specifies that criteria. However, if a small percentage of the comparable studies utilized the index criterion, this can indicate that the criterion is potentially incorrect or incomplete. In embodiments, any number of factors can be evaluated to determine a confidence measure for each specific criterion. In an embodiment, the confidence measure indicates a level of confidence that the specified criterion was actually used to define the participant cohort, or is actually applicable to define the cohort of patients who the study applies to.

In an embodiment, once the criteria have been evaluated, their confidence measures are incorporated into the knowledge graph for further use. When selecting or ranking therapies for an index patient, the therapies can be evaluated in light of these confidence values. For example, in one embodiment, the stated efficacies or comparisons made in each document are aggregated to determine an overall predicted efficacy of each therapy with respect to the index patient. In an embodiment, the contribution of an individual document (e.g., the weight of the document) to the overall score for the therapy is based at least in part on how closely the index patient's attributes align with the stated criteria. In embodiments of the present disclosure, the documents are further weighted based on the confidence values associated with each criteria. For example, if the index patient aligns with all but one criterion, the document may be given a reduced weight. However, if the misaligned criterion is associated with a relatively low confidence, the weight of the document will be greater than if the mismatched criterion was associated with a high confidence.

In some embodiments of the present disclosure, techniques for cognitive analysis, representation, and interpretation of published literature are provided. In one embodiment, a corpus of medical literature is parsed and analyzed to identify and extract comparative statements or opinions made by the authors of the paper. For example, in a conclusion or summary, the authors may indicate that a particular therapy showed improved results, as compared to one or more other therapies (or as compared to the known or popular literature and practices). These conclusions are provided in natural language text, and are rarely structured in a way that allows for easy ingestion of the information. Embodiments of the present disclosure are discussed with reference to medical literature. However, these examples are not limiting on the present disclosure, and one of skill in the art will recognize other domains and literature that the present embodiments can be applied to.

In one embodiment, these comparative statements are interpreted to determine a sentiment of the statement, and the relative efficacy of each therapy discussed. In some embodiments, a data structure, referred to herein as a relative efficacy structure or RES, is generated to capture the natural language comparative statement in a useful format. For example, in one embodiment, the RES has a number of dimensions, including the directionality of the comparison (e.g., which therapy is superior), the magnitude of the difference, the particular outcome the statement refers to (e.g., survival, progression-free survival, remission, etc.), qualifiers of the statement (e.g., limitations or specifications), and the like. In an embodiment, each RES is also associated with a weight, which is based on a variety of factors related to the underlying comparative statement and the nature of the article it is contained in.

In one embodiment, if a comparison is found in one direction (e.g., that treatment A is better than treatment B), a complementary RES is created in the opposite direction (e.g., indicating that treatment B is worse than treatment A). In this way, queries for information for a given treatment or therapy can identify all documents that involve the therapy, regardless of whether the document deemed the therapy to be superior or inferior.

In some embodiments, a knowledge graph can be generated based on the determined relationships extracted from one or more published document. For example, in one embodiment, each node in the knowledge graph corresponds to a particular therapy, and each edge corresponds to one or more RESs. In this way, the knowledge graph can be interrogated or searched to identify optimal treatment options for a given patient, based on a tremendous variety of medical literature. In such an embodiment, patient outcomes are improved, as the current state of the literature can be captured and ingested into the knowledge graph rapidly, reducing or eliminating the need for SME review. Further, in embodiments, the RESs provide additional insight and knowledge that is not accessible or present in existing solutions. Thus, embodiments of the present disclosure enable high-precision searching, and allow users to analyze the literature at a more granular level.

In some embodiments, users can search or query the knowledge graph based on therapies, cohorts, disorders, and the like, to return a subset of the graph that is relevant to the search. Further, in some embodiments, nodes and/or connections can be selected to retrieve a link to any documents or published literature that was analyzed to create the node or edge. In this way, users can readily access the relevant literature, if they wish to investigate further or obtain more information about why the topology of the graph is shaped as it is, as well as why particular connections exist.

Embodiments of the present disclosure can be applied to extract and interpret comparative statements made in any field. In one embodiment, medical literature (e.g., published studies, trials, experiments, and the like) is ingested. In some embodiments, the literature is analyzed to identify comparisons or statements about relative efficacy between therapy options. In an embodiment, a therapy is any treatment used to treat a disorder. As used herein, therapies can include drugs, medications, exercises, surgeries, use of equipment, prescribed activities, and the like. Further, in embodiments, therapies can include refraining from certain activities and withdrawing or reducing treatments. Additionally, in embodiments, a therapy may include multiple treatments or prescribed activities (e.g., multiple medications). As used herein, a medical disorder can include any illness or medical condition, including but not limited to mental or physical disease, sickness, disability, infection, symptoms, conditions, or statuses.

FIG. 1 illustrates a workflow 100 for cognitively determining the relative efficacy of therapies, according to one embodiment disclosed herein. In the illustrated embodiment, a Cognitive Interpretation Application 105 analyzes documents to extract Comparative Statements 130 and generate RESs 140, and a Knowledge Graph Component 110 analyzes these RESs 140 to generate a Knowledge Graph 150. In some embodiments, a Knowledge Graph 150 is generated to aid visualization or understanding of the literature (although it may not actually be displayed). In some embodiments, however, the knowledge graph is not created, and the RESs 140 are used for other purposes. That is, in some embodiments, the generated RESs are usable or searchable by other systems or components, and can be utilized to aid understanding and improve treatment selection, without the construction of a knowledge graph.

In the illustrated workflow 100, the Cognitive Interpretation Application 105 analyzes a Corpus 115 of documents to perform Comparison Extraction 120. In an embodiment, the Corpus 115 includes documents which include at least some portion of natural language text, which may or may not have comparative statements by the author(s). In some embodiments, the Corpus 115 corresponds to a particular domain of interest to a user. For example, in one embodiment, a larger corpus or collection of documents is searched to identify a subset of the documents that relate to a particular disorder, therapy, or set of disorders or therapies. In such an embodiment, this subset of documents makes up the Corpus 115. In some embodiments, the workflow 100 is performed on multiple corpora (e.g., once for each therapy or disorder).

In an embodiment, the Comparison Extraction 120 comprises utilizing one or more natural language processing (NLP) techniques to identify comparative statements in the text included in the Corpus 115. For example, in one embodiment, the Cognitive Interpretation Application 105 searches for comparative language (such as "superior," "better," "worse," "improved," and the like). In some embodiments, the Cognitive Interpretation Application 105 analyzes predefined sections of the documents to identify these comparative statements (e.g., the abstract, conclusion, methods, discussion, etc.). That is, in an embodiment, a user or administrator can specify portions or sections in the documents that should be analyzed. In other embodiments, the Cognitive Interpretation Application 105 analyzes the full text of the document. In one embodiment, the Cognitive Interpretation Application 105 first searches the identified sections (as identified by their headings or by metadata tags), and only parses the rest of the document if the specified section(s) do not include any comparative statements (or if the specified section(s) cannot be found or do not exist in the document).

In some embodiments, the Comparison Extraction 120 also includes remedying unknown terms in the statement, such as through disambiguation and acronym resolution. For example, if the comparative statement includes an acronym, in one embodiment, the Cognitive Interpretation Application 105 can expand the acronym. Similarly, if the statement includes ambiguous or general language (such as, "all treatments studied herein", "with respect to the relevant cohort," or "generic chemotherapy drugs"), the Cognitive Interpretation Application 105 can determine a meaning for the terms. In some embodiments, the Cognitive Interpretation Application 105 first parses the selected document to identify the meaning of the term. That is, the Cognitive Interpretation Application 105 attempts to find meaning for the unknown term by analyzing the text of the document in which the comparative statement was found using NLP techniques. If no satisfactory disambiguation is found (e.g., the confidence level of any potential disambiguations is below a threshold), the Cognitive Interpretation Application 105 can access other literature (or one or more knowledge graphs) to disambiguate the term. In some embodiments, if the true meaning is not found within the corresponding document, the confidence or weight of the extracted comparison is reduced.

In some embodiments, Comparison Extraction 120 includes annotation of the extracted comparative statements. For example, in one embodiment, the Cognitive Interpretation Application 105 utilizes one or more NLP techniques to identify the therapy or therapies involved in the statement, the qualifier or comparative term utilized, and the like. In some embodiments, the Cognitive Interpretation Application 105 also determines the cohort(s) to which the statement (s) apply, as discussed in more detail below. Additionally, in some embodiments, the Cognitive Interpretation Application 105 determines characteristics of the comparative statements, such as where in the text it was located (e.g., which section it was found in), the publication date of the document, whether the document has been peer-reviewed, an identity of the publisher or entity that provided the document, and the like.

In the illustrated embodiment, the Cognitive Interpretation Application 105 stores the extracted comparisons (e.g., the natural language text) in a data store for Comparative Statements 130. In some embodiments, these stored Comparative Statements 130 are annotated to identify the relevant therapies, qualifiers, and the like. In some embodiments, the Comparative Statements 130 also indicate the disorder that is relevant to the comparison. In other embodiments, the disorder is described by the cohort and/or cohort qualifiers. In embodiments, the Comparative Statements 130 can be stored locally by the Cognitive Interpretation Application 105, or in one or more remote storage locations (such as in the cloud). As illustrated, the Cognitive Interpretation Application 105 then performs Sentiment Analysis 135 on the extracted Comparative Statements 130, to generate a set of RESs 140. In an embodiment, this Sentiment Analysis 135 includes classifying each statement as positive, negative, or neutral with respect to each of the implicated therapies. In some embodiments, the Cognitive Interpretation Application 105 also determines a degree of the sentiment (based on, for example, the strength of the language or term used). Further, in some embodiments, the RESs 140 include an indication as to which outcome or outcome type the comparison relates to (e.g., overall survival, progression-free survival, etc.).

In some embodiments, the RESs 140 include an indication as to the therapies involved, the relevant cohort, and the like. In one embodiment, each RES 140 corresponds to a particular Comparative Statement 130. In one embodiment, each RES 140 is weighted based on a variety of factors. For example, in an embodiment, the weighting factors include how recently the corresponding document was published, whether the document has been peer-reviewed, the identity of the publisher or provider for the document, the number of patients evaluated in the clinical study, and the like. In one embodiment, publishers are associated with predefined weights or strengths, based on their prestige or trustworthiness. In some embodiments, the Cognitive Interpretation Application 105 weights each RES 140 based on a confidence level as well. In one embodiment, this confidence level is based in part on a confidence value returned by the NLP models. Further, in an embodiment, the confidence is adjusted based on where in the document the corresponding Comparative Statement 130 was found. For example, a comparison found in the abstract or conclusion can be given a higher weight, while a comparison found elsewhere in the document can be given a lower weight.

In the illustrated embodiment, the Knowledge Graph Component 110 retrieves these RESs 140 from the data store, and performs Graph Generation 150 to generate a Knowledge Graph 155. In an embodiment, each node in the Knowledge Graph 150 is a therapy (or combination of therapies), and each edge is based on the determined relationships and relative efficacies (e.g., the RESs 140). In one embodiment, the Knowledge Graph Component 110 adds an edge or connection for each determined RESs 140 (e.g., for each comparative statement found). In some embodiments, the Knowledge Graph Component 110 aggregates the comparisons. For example, in an embodiment, for each outcome type and cohort combination, the Knowledge Graph Component 110 can aggregate the corresponding RESs 140, in order to determine an overall relative efficacy for the therapies, with respect to the cohort and outcome. In some embodiments, this aggregation is based in part on the weights of each comparison, as discussed above.

Although not depicted in the illustrated embodiment, in some embodiments, the Cognitive Interpretation Application 105 also identifies statements relating to the efficacy or outcomes of a therapy, even in the absence of a comparison between therapies. In such an embodiment, the Cognitive Interpretation Application 105 can also perform Sentiment Analysis 135 on the non-comparative statements to determine whether the therapy is being referred to in a positive, neutral, or negative manner. In some embodiments, the Cognitive Interpretation Application 105 also determines the efficacy and/or outcomes of the therapy, if available in the Corpus 115. For example, in such an embodiment, the Cognitive Interpretation Application 105 can determine what percentages of patients benefited (with respect to each potential outcome), the magnitude of the benefits, and the like. In an embodiment, the Knowledge Graph Component 110 then incorporates these non-comparative statements into the Knowledge Graph 155 (e.g., by adding or refining a node corresponding to the therapy being discussed).

Figure 2:
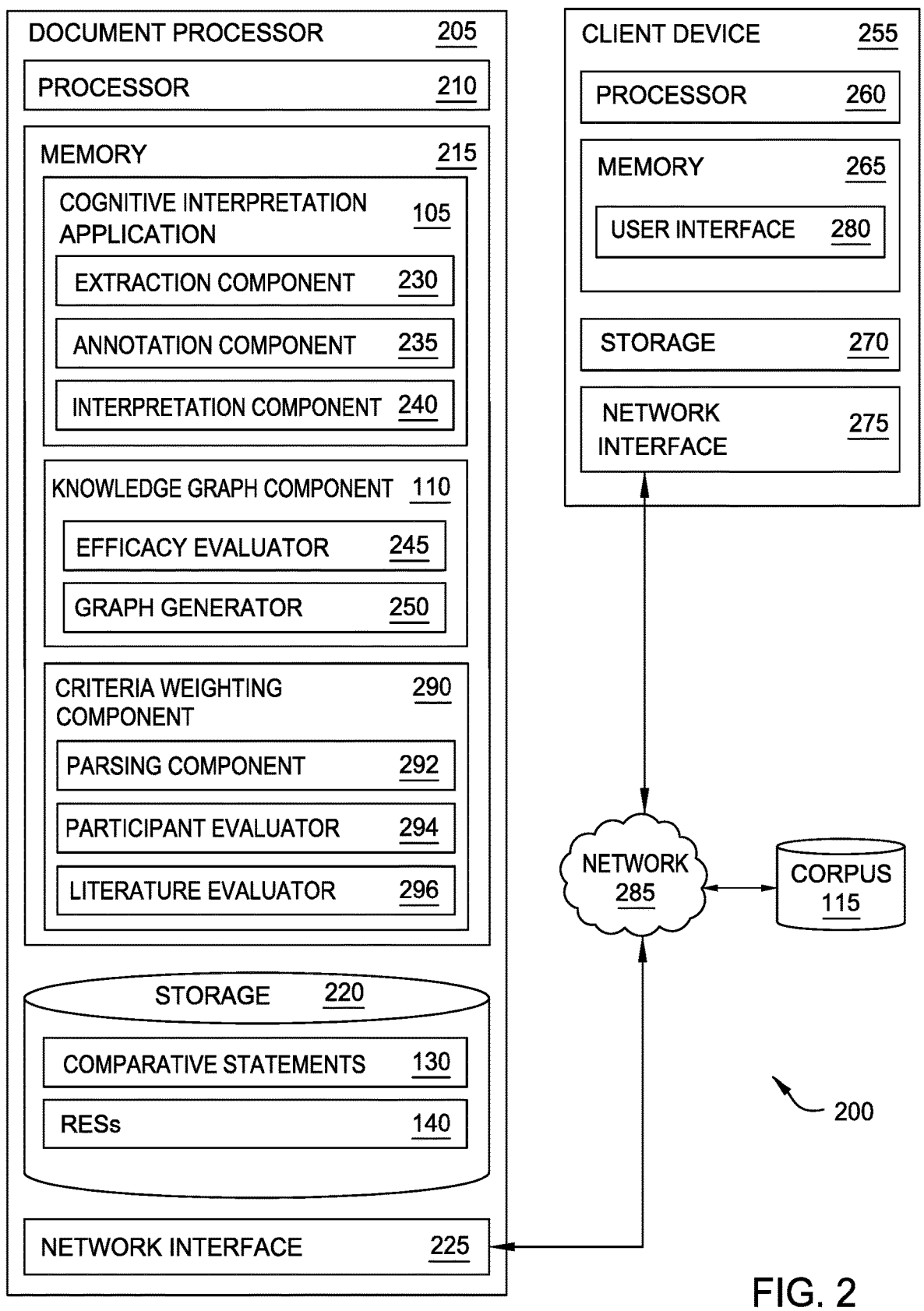
FIG. 2 is a block diagram of a system configured to cognitively determine the relative efficacy of therapies, according to one embodiment disclosed herein.

FIG. 2 is a block diagram of a system 200 configured to cognitively determine the relative efficacy of therapies, according to one embodiment disclosed herein. In the illustrated embodiment, the system 200 includes a Document Processor 205, a Client Device 255, and a Corpus 115.

Although illustrated as discrete components, in embodiments, the Document Processor 205, Client Device 255, and Corpus 115 may operate or reside on a single device, or may be distributed across any number of devices. As illustrated, the Document Processor 205, Client Device 255, and Corpus 115 are communicatively linked through a Network 285. In one embodiment, the Network 285 is the Internet. Additionally, though a single Corpus 115 is illustrated, in embodiments, any number of corpora may be analyzed by the Document Processor 205.

As illustrated, the Document Processor 205 includes a Processor 210, a Memory 215, and Storage 220. In the illustrated embodiment, Processor 210 retrieves and executes programming instructions stored in Memory 215 as well as stores and retrieves application data residing in Storage 220. Processor 210 is representative of a single CPU, multiple CPUs, a single CPU having multiple processing cores, and the like. Memory 215 is generally included to be representative of a random access memory. Storage 220 may be a disk drive or flash-based storage device, and may include fixed and/or removable storage devices, such as fixed disk drives, removable memory cards, or optical storage, network attached storage (NAS), or storage area-network (SAN). Via the Network Interface 225, the Document Processor 205 can be communicatively coupled with corpuses of documents (such as Corpus 115), Client Devices 255, and the like.

In the illustrated embodiment, the Storage 220 of the Document Processor 205 includes a set of Comparative Statements 130 and RESs 140. In some embodiments, as discussed above, the Comparative Statements 130 and/or RESs 140 may be stored in one or more remote storage locations, such as in the cloud. Further, in some embodiments, the Storage 220 includes non-comparative statements as well. As discussed above, in an embodiment, the Comparative Statements 130 are annotated natural language text extracts from documents in the Corpus 115. In one embodiment, each Comparative Statement 130 includes a comparison or opinion of the author of the corresponding document. In some embodiments, the annotations indicate the qualifier or comparator used by the author, the therapies implicated by the statement, the cohort or cohort qualifiers that limit the applicability of the comparison, and the like. Further, in some embodiments, the Comparative Statements 130 include publication characteristics of the statements, such as the location in their corresponding documents where they were found, the date of the publication, the entity that published it, and the like. Additionally, in one embodiment, the Comparative Statements 130 include an indication as to the confidence value that the NLP model(s) generated when parsing the statements.

As discussed above, in one embodiment, each RES 140 is a data structure representing a particular Comparative Statement 130. In some embodiments, each RES 140 indicates the therapies involved, the directionality or sentiment of the comparison, the cohort implicated, and the like. Further, in an embodiment, each RES 140 includes a weight, which can be based on a variety of factors including the publication characteristics of the underlying Comparative Statement 130, the confidence of the NLP model(s), and the like. In some embodiments, the RESs 140 are configured to be searchable, such that other systems or components (such as the Knowledge Graph Component 110) can readily access the information, and obtain an up-to-date and comprehensive understanding of the current state of the literature.

In the illustrated embodiment, the Memory 215 of the Document Processor 205 includes a Cognitive Interpretation Application 105, a Knowledge Graph Component 110, and a Criteria Weighting Component 290. The Cognitive Interpretation Application 105 includes an Extraction Component 230, an Annotation Component 235, and an Interpretation Component 240. Although depicted as discrete components for illustration, in embodiments, the operations and functionality of the Extraction Component 230, Annotation Component 235, and Interpretation Component 240 can be combined or divided across any number of components. Further, although depicted as software components residing in Memory 215, in embodiments, the operations and functionality of the Extraction Component 230, Annotation Component 235, and Interpretation Component 240 can be implemented using hardware, software, or a combination of hardware and software.

In an embodiment, the Extraction Component 230 identifies and extracts statements that include comparisons between therapies or treatment options from documents in the Corpus 115, as discussed above. In some embodiments, the Extraction Component 230 utilizes one or more NLP techniques or models to identify the relevant text. Further, in an embodiment, the Annotation Component 235 annotates the extracted statements. In one embodiment, the Annotation Component 235 utilizes predefined rules, and/or additional NLP models and/or techniques to annotate the statements. These annotated statements are then stored in the Comparative Statements 130. In this way, the textual comparisons found in the Corpus 115 are organized and represented in the Storage 220.

In the illustrated embodiment, the Interpretation Component 240 retrieves these Comparative Statements 130 and performs logical interpretation or sentiment analysis on them. In one embodiment, the Interpretation Component 240 classifies each Comparative Statement 130 as positive, negative, or neutral, with respect to each pair of involved therapies or treatments. For example, if the statement is that "treatment A led to better results than treatment B," the Interpretation Component 240 can determine that the comparison is positive with respect to treatment A, and negative with respect to treatment B. Similarly, if the statement is "treatments C and D were both inferior to treatment E," the Interpretation Component 240 determines that, as between therapies C and D, the sentiment is "neutral" or equal. However, as between treatment E and treatments C and D, the sentiment is positive. In this way, the Interpretation Component 240 determines the efficacy of each therapy, as compared to one or more other therapies in the statement.

In one embodiment, the Interpretation Component 240 also generates RESs 140 based on this analysis, as discussed below in more detail. That is, in an embodiment, the Interpretation Component 240 generates an organized and defined data structure that includes the relevant information from the textual Comparative Statement 130. In some embodiments, the Interpretation Component 240 generates a single RES 140 for each Comparative Statement 130. For example, in such an embodiment, if the sentiment is that treatment A is better than treatment B, the Interpretation Component 240 will generate a RES 140 indicating that treatment A is positive with respect to treatment B. In some embodiments, the Interpretation Component 240 also generates a second RES 140 indicating that treatment B is negative with respect to treatment A.

In the illustrated embodiment, the Knowledge Graph Component 110 generally retrieves the RESs 140 from Storage 220, and generates one or more knowledge graphs. As illustrated, the Knowledge Graph Component 110 includes an Efficacy Evaluator 245, and a Graph Generator 250. Although depicted as discrete components for illustration, in embodiments, the operations and functionality of the Efficacy Evaluator 245 and Graph Generator 250 can be combined or divided across any number of components. Further, although depicted as software components residing in Memory 215, in embodiments, the operations and functionality of the Efficacy Evaluator 245 and Graph Generator 250 can be implemented using hardware, software, or a combination of hardware and software. In an embodiment, the Efficacy Evaluator 245 retrieves and evaluates the RESs 140. For example, in one embodiment, the Efficacy Evaluator 245 searches for RESs 140 relating to one or more disorders or therapies that a user or administrator has selected. In other embodiments, the Efficacy Evaluator 245 retrieves and evaluates all available RESs 140. In an embodiment, the evaluation includes determining whether each RES 140 is already included in the knowledge graph.

Additionally, in some embodiments, the Efficacy Evaluator 245 aggregates the RESs 140 as appropriate, to determine an overall relative efficacy for each set of therapies. For example, in one embodiment, the Efficacy Evaluator 245 identifies RESs 140 with the same endpoints (e.g., that involve the same set of therapies) and aggregates them based on their respective weights to generate an overall relative efficacy between the therapies. In an embodiment, the Graph Generator 250 generates, inserts, and updates or refines nodes and edges in the knowledge graph, based on the evaluation provided by the Efficacy Evaluator 245. In some embodiments, the Graph Generator 250 and/or Efficacy Evaluator 245 aggregate the data by identifying all RESs 140 involving the same pair of therapies and including them in the graph, in order to capture all available evidence that compares the therapies without attempting to establish whether one is overall superior to the other.

In the illustrated embodiment, the Criteria Weighting Component 290 includes a Parsing Component 292, a Participant Evaluator 294, and a Literature Evaluator 296. Although depicted as discrete components for illustration, in embodiments, the operations and functionality of the Parsing Component 292, Participant Evaluator 294, and Literature Evaluator 296 can be combined or divided across any number of components. Further, although depicted as software components residing in Memory 215, in embodiments, the operations and functionality of the Parsing Component 292, Participant Evaluator 294, and Literature Evaluator 296 can be implemented using hardware, software, or a combination of hardware and software.

In an embodiment, the Criteria Weighting Component 290 analyzes and evaluates stated criteria in order to determine a confidence measure for each. In one embodiment, the confidence measure for a particular criterion indicates the likelihood that the criterion is accurate. In embodiments, the criterion is less likely to be accurate if it is unclear or ambiguous, inconsistent with other parts of the document or with the published literature, excludes patients who participated in the underlying study or trial, and the like. In an embodiment, this confidence value is incorporated into the knowledge graph, such that it can be considered when evaluating the graph and/or the literature. For example, if a criterion is associated with a relatively low confidence, it will be assigned a relatively lower weight when determining a weight or score for the document, with respect to the index patient.

In the illustrated embodiment, the Parsing Component 292 evaluates the text of the specified criteria using one or more NLP techniques to identify ambiguities, inconsistencies, and contradictions. Further, in some embodiments, the Parsing Component 292 similarly analyzes the title, description, or other text associated with the corresponding document. In such an embodiment, the Parsing Component 292 can determine whether the criteria conflict with the other text, which leads to reduced confidence. In one embodiment, the Parsing Component 292 further compares each criterion to each other criteria in the index document, in order to determine whether any of the criteria conflict or contradict each other. In this way, the Parsing Component 292 determines the semantic meaning of the criteria, in order to generate a confidence measure indicating the accuracy of each criterion.

In an embodiment, the Participant Evaluator 294 analyzes attributes of the participants associated with the document, in order to generate or modify the confidence measure for each criterion. In one embodiment, Participant Evaluator 294 determines, for each stated criterion, whether the actual participants align with the criterion. In some embodiments, the Participant Evaluator 294 determines whether any participants do not match the criterion. If so, the confidence of the criterion is reduced. In one embodiment, the Participant Evaluator 294 modifies or generates the confidence measure based on a number or percentage of participants who do not align with the criterion. In embodiments, the confidence of the criterion is inversely related to the number or percentage of patients who do not satisfy the criterion. For example, if two of the participants do not meet the criterion, the Participant Evaluator 294 can assign a relatively higher confidence than if ten participants do not satisfy the criterion.

In the illustrated embodiment, the Literature Evaluator 296 analyzes other related or similar documents, in order to generate or modify the confidence measure for each criterion in the index document. In one embodiment, the Literature Evaluator 296 identifies similar documents based on the disorder(s) associated with the index document (e.g., the disorder being studied), the therapy or therapies being evaluated by the index document, and the like. In some embodiments, the Literature Evaluator 296 aggregates the criteria specified in each identified similar document, and determines a confidence measure for each criteria specified in the index document based on these aggregated criteria. For example, in one embodiment, if one or more other studies specify the same criterion, the confidence measure of the criterion may be relatively higher than if no other documents have used the same criterion. Further, in some embodiments, the confidence measure is directly related to the number or percentage of the existing literature that state the same criterion, such that criteria that are frequently specified (e.g., where a significant portion of the published literature use the same criterion) are scored relatively higher than criteria that are present in the literature, but that are infrequently used.

In the illustrated embodiment, the Client Device 255 includes a Processor 260, a Memory 265, and Storage 270. In the illustrated embodiment, Processor 260 retrieves and executes programming instructions stored in Memory 265 as well as stores and retrieves application data residing in Storage 270. Processor 260 is representative of a single CPU, multiple CPUs, a single CPU having multiple processing cores, and the like. Memory 265 is generally included to be representative of a random access memory. Storage 270 may be a disk drive or flash-based storage device, and may include fixed and/or removable storage devices, such as fixed disk drives, removable memory cards, or optical storage, network attached storage (NAS), or storage area-network (SAN). Via the Network Interface 275, the Client Device 255 can be communicatively coupled with corpuses of documents (such as Corpus 115), Document Processor 205, and the like.

As illustrated, the Memory 265 of the Client Device 255 includes a User Interface 280 for interacting with the Corpus 115 and/or Document Processor 205. In an embodiment, the User Interface 280 includes a graphical user interface (GUI) that lets users or administrators retrieve and review documents in the Corpus 115. In some embodiments, the User Interface 280 also allows the user to select a subset of the Corpus 115 (e.g., via search queries) to be processed by the Document Processor 205.

Although not illustrated, in embodiments, the Cognitive Interpretation Application 105, Knowledge Graph Component 110, and Criteria Weighting Component 290 each provide one or more application programming interfaces (APIs) that allow the user (through the User Interface 280) to control the operations of the components. For example, in an embodiment, the user can use the User Interface 280 and APIs to indicate the set of documents to be analyzed, and to adjust any settings or configurations of the Cognitive Interpretation Application 105. Further, in an embodiment, the User Interface 280 and APIs enable the user to review the Comparative Statements 130 and/or RESs 140. Additionally, in an embodiment, the User Interface 280 and APIs allow the user to direct the Knowledge Graph Component 110 to generate one or more knowledge graphs based on the RESs 140, and to analyze and parse the generated graphs. Additionally, in an embodiment, the APIs allow the user to generate confidence values for criteria, and to generate therapy scores or rankings based in part on these confidence values.

Figure 3A:
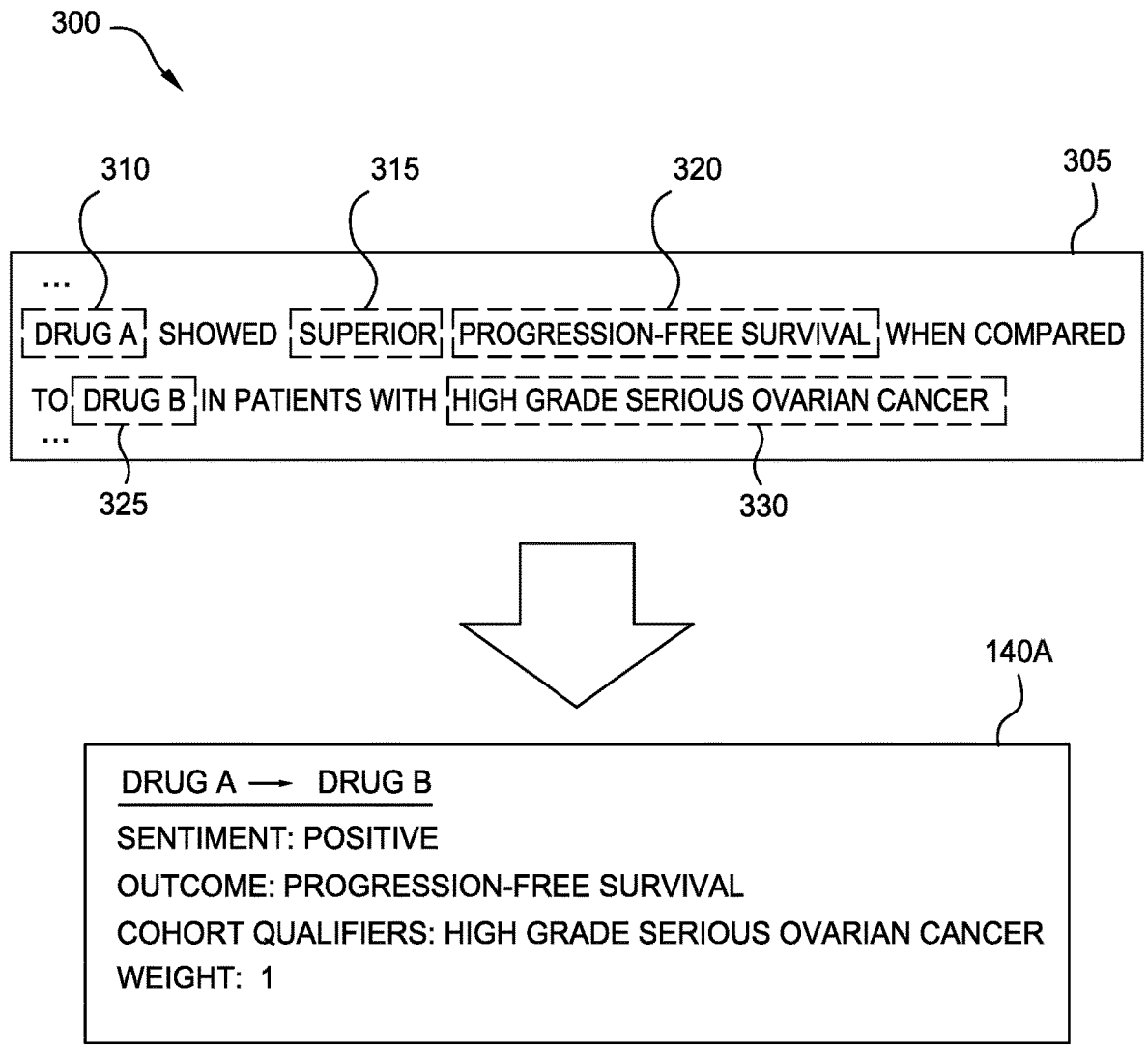
FIG. 3A is a workflow for determining the efficacy for a therapy, as compared to a different therapy, according to one embodiment disclosed herein.

FIG. 3A illustrates a workflow 300 for determining the efficacy for a therapy, as compared to a different therapy, according to one embodiment disclosed herein. In the illustrated workflow 300, a comparative statement (included in an Excerpt 305) is annotated with Annotations 310, 315, 320, 325, and 330. As illustrated by the ellipses above and below the comparative statement, the original document can be any size or length. In an embodiment, the Excerpt 305 was extracted from a document (e.g., by the Extraction Component 230) based on determining that it included a comparative statement.

In the illustrated embodiment, the Excerpt 305 was annotated by the Annotation Component 235, using one or more NLP techniques. As illustrated, Annotations 310 and 325 indicate the therapies mentioned or implicated by the statement. In one embodiment, these therapies are identified based on identifying the subject and object of the statement. Further, as illustrated, the Annotation 320 indicates the outcome (also referred to as the type) that is relevant to the statement. That is, in the illustrated embodiment, the Excerpt 305 discusses the relative efficacy of Drug A and Drug B, with respect to progression-free survival. Additionally, the Annotation 315 indicates the comparator (also referred to as qualifier or type qualifier), which indicates the comparison or statement being made (e.g., that the outcome, progression-free survival, was "superior."). Finally, as illustrated, the Annotation 330 corresponds to the cohort (or cohort qualifier) that the statement applies to.

In the illustrated embodiment, each of the relevant factors (e.g., Annotations 310, 315, 320, 325, and 330) are included within the same Excerpt 305. In embodiments, however, one or more of the relevant pieces of information can be located outside of the Excerpt 305. For example, in an embodiment, the cohort may be specified elsewhere in the document, and not explicitly given in the Excerpt 305. Similarly, one or more of the therapies or outcomes can be given elsewhere. For example, suppose the statement included "therapy Y led to the best results for the patients included in this study." In such an embodiment, the Extraction Component 230 and/or Annotation Component 235 can look elsewhere to determine the other therapy, the cohort, and the particular outcome type. Further, in an embodiment, the excerpt may only summarize one of the therapies in question and the Annotation Component 235 may look elsewhere to determine the complete definition of the therapy. For example, an excerpt may refer to "drug X-based therapy," where all of the components of this therapy are defined elsewhere in the document.

For example, the other therapies being tested may be listed in an introductory section, the cohort can be determined based on analyzing the patients involved, and the outcome of interest can be identified based on other sections of the document. In some embodiments, if the relevant information is not contained within the Excerpt 305, the confidence or weight of the comparative statement is reduced. In some embodiments, the Extraction Component 230 and/or Annotation Component 235 identify both the cohort (e.g., the patient population being studied) as well as cohort qualifiers (e.g., additional restrictions or limitations defining the group to whom the comparison is relevant). In one embodiments, the relevant cohort can identified based on other portions of the document (e.g., based on the abstract or study definitions). For example, a section of the document can indicate that the patients studied included females, aged 65-80, with hypertension. Additionally, the cohort qualifier ("high grade serious ovarian cancer") further restricts or limits the cohort to which the comparison is applicable.

As illustrated, the Cognitive Interpretation Component 105 (e.g., the Sentiment Component 240) then generates a RES 140A, based on the comparative statement. In the illustrated embodiment, as indicated by the arrow from Drug A to Drug B, the RES 140A indicates the relative efficacy of Drug A, as compared to Drug B. As illustrated, the sentiment is "positive," indicating that Drug A is better than Drug B with respect to the indicated cohort and the indicated outcome. Further, as illustrated, the outcome is "progression-free survival," and the cohort is individuals with "high grade serious ovarian cancer." As discussed above, in embodiments, this cohort can include additional attributes or definition, in combination with the cohort qualifiers found in the statement. Additionally, in the illustrated embodiment, the RES 140A includes a weight. In embodiments, this weight is based on a variety of factors, including the confidence of the NLP, the publication characteristics of the document, and the like.

Figure 3B:
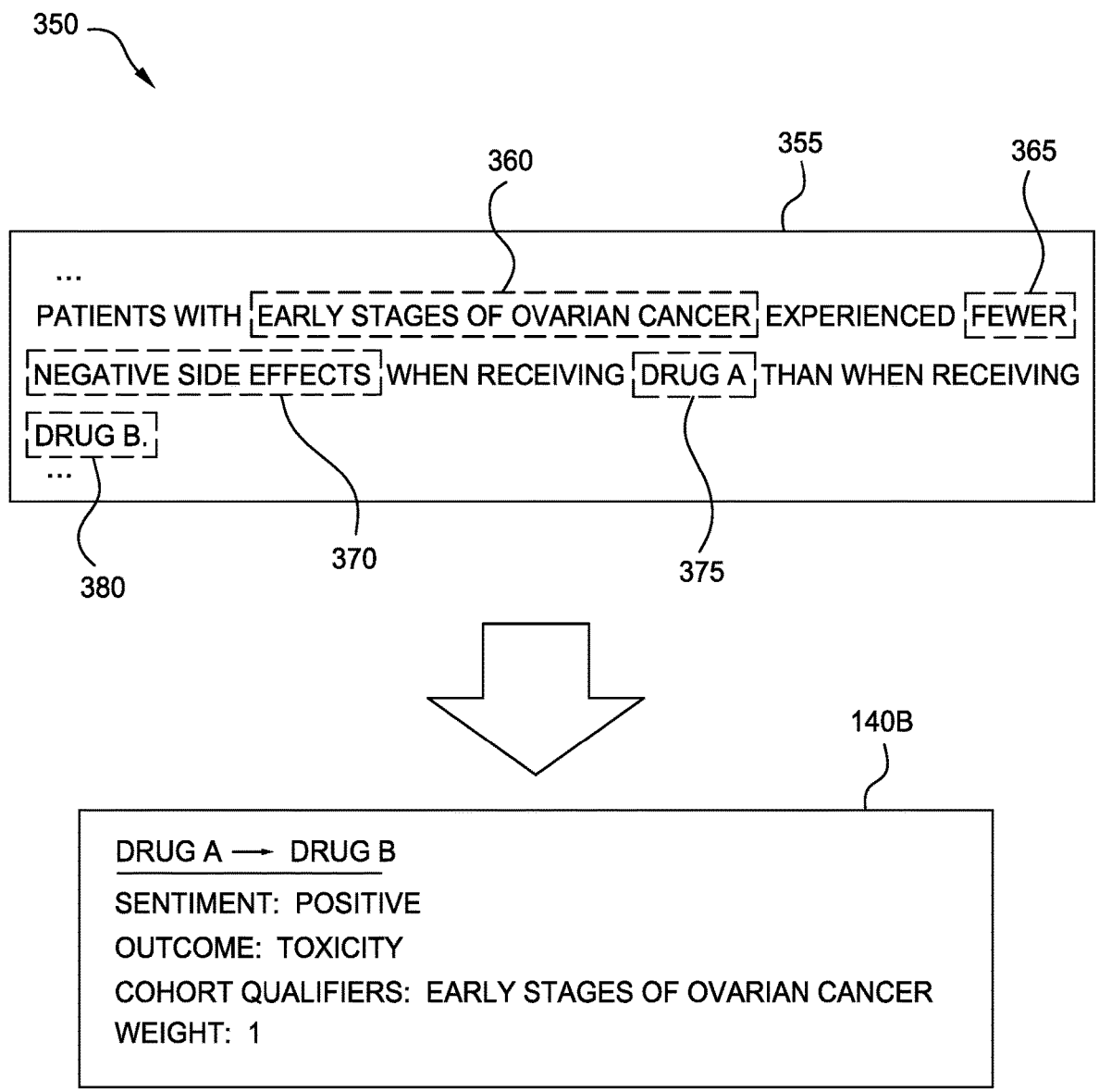
FIG. 3B illustrates a workflow for determining the efficacy for a therapy, as compared to a different therapy, according to one embodiment disclosed herein.

FIG. 3B illustrates a workflow 350 for determining the efficacy for a therapy, as compared to a different therapy, according to one embodiment disclosed herein. In the illustrated workflow 350, a comparative statement (included in an Excerpt 355) is annotated with Annotations 360, 365, 370, 375, and 380. As illustrated by the ellipses above and below the comparative statement, the original document can be any size or length. In an embodiment, the Excerpt 355 was extracted from a document (e.g., by the Extraction Component 230) based on determining that it included a comparative statement.

In an embodiment, the Excerpt 355 was annotated by the Annotation Component 235, using one or more NLP techniques. In the illustrated embodiment, Annotations 375 and 380 indicate the therapies mentioned or implicated by the statement. In one embodiment, these therapies are identified using the NLP models or techniques. Further, as illustrated, the Annotation 370 indicates the outcome of interest (also referred to as the type) that is relevant to the statement. That is, in the illustrated embodiment, the Excerpt 355 discusses the relative efficacy of Drug A and Drug B, with respect to negative side effects. Additionally, the Annotation 365 indicates the comparator (also referred to as qualifier or type qualifier), which indicates the comparison or statement being made (e.g., that the outcome, negative side effects, was "fewer."). Finally, as illustrated, the Annotation 360 corresponds to the cohort (or cohort qualifier) that the statement applies to.

As illustrated, the Cognitive Interpretation Component 105 (e.g., the Sentiment Component 240) then generates a RES 140B, based on the comparative statement. In the illustrated embodiment, as indicated by the arrow from Drug A to Drug B, the RES 140B indicates the relative efficacy of Drug A, as compared to Drug B. As illustrated, the sentiment is "positive," indicating that Drug A is better than Drug B with respect to the indicated cohort and the indicated outcome. That is, because the outcome itself is negative, the Sentiment Component 240 determines that a "worse" result in terms of the number or magnitude of side effects is, in fact, a positive result. Further, as illustrated, the outcome is "toxicity," and the cohort is individuals with "early stages of ovarian cancer." Additionally, in the illustrated embodiment, the RES 140B includes a weight. In embodiments, this weight is based on a variety of factors, including the confidence of the NLP, the publication characteristics of the document, and the like.

Figure 4:
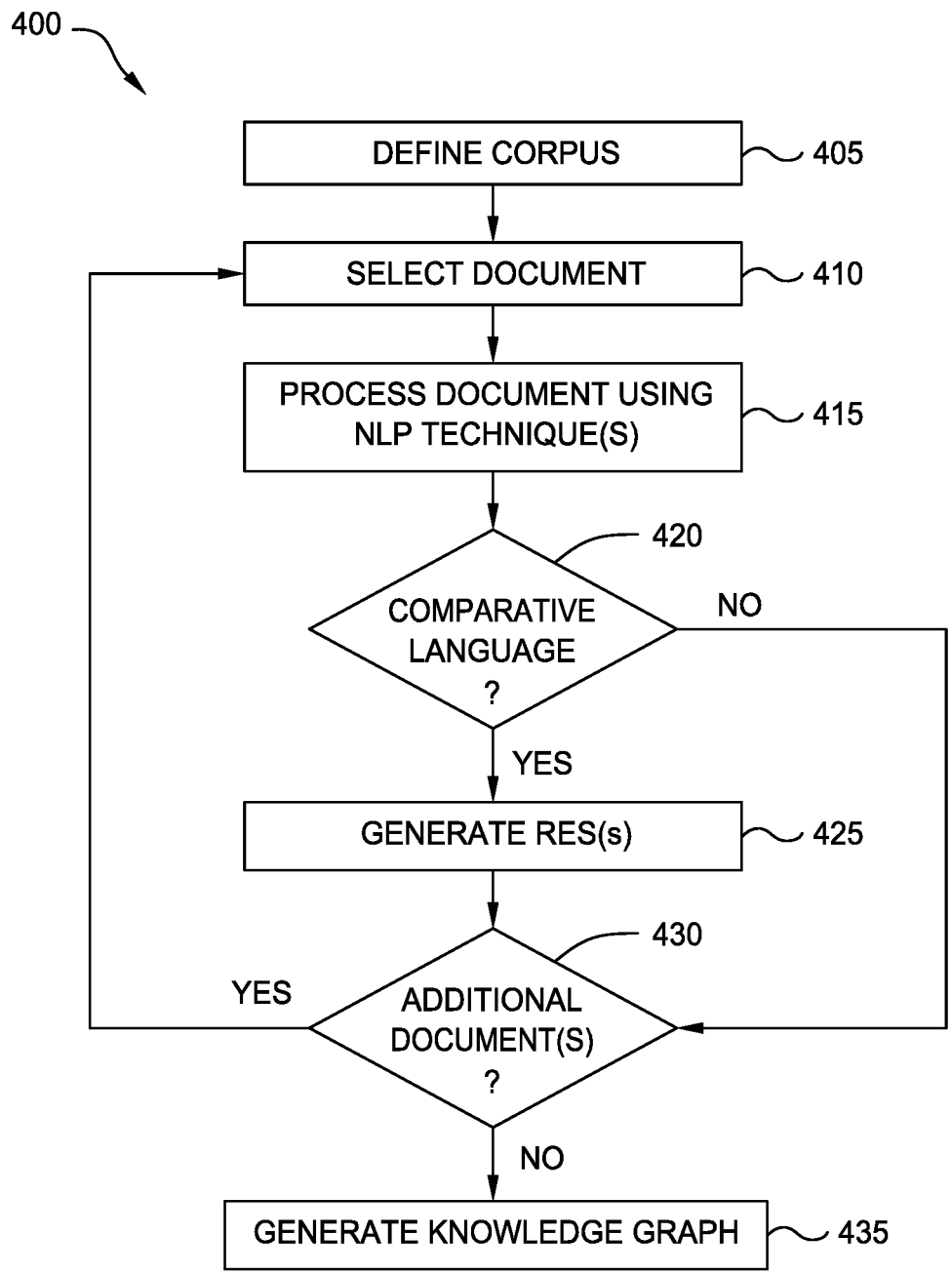
FIG. 4 illustrates a flow diagram illustrating a method for determining relative efficacies of various therapies, according to one embodiment disclosed herein.

FIG. 4 is a flow diagram illustrating a method 400 for determining relative efficacies of various therapies, according to one embodiment disclosed herein. The method 400 begins at block 405, where the Cognitive Interpretation Application 105 defines the relevant corpus. In one embodiment, this is based on a corpus indicated by the user or administrator. In some embodiments, the Cognitive Interpretation Application 105 receives one or more search terms, and builds the relevant corpus by searching or querying a larger corpus based on the search terms. In some embodiments, the Cognitive Interpretation Application 105 determines a set of documents in the identified corpus or subcorpus that have not yet been processed or ingested. For example, in one embodiment, a user can indicate a disorder or search term, and the Cognitive Interpretation Application 105 can first identify documents relating to the indicated terms, and then identify documents in the corpus that have not already been processed and ingested. In this way, the Cognitive Interpretation Application 105 can selectively analyze new documents in order to update and refine the knowledge base. Once the relevant corpus has been defined, the method 400 proceeds to block 410.

At block 410, the Cognitive Interpretation Application 105 selects a document from the corpus. At block 415, the Cognitive Interpretation Application 105 processes the all or a portion of the selected document using one or more NLP techniques. As discussed above, in some embodiments, the Cognitive Interpretation Application 105 analyzes specified portions of each document. In some embodiments, if no comparisons are found (or if one or more identified comparative statements are missing information or detail), the Cognitive Interpretation Application 105 can process additional sections or text. In one embodiment, the Cognitive Interpretation Application 105 also annotates the extracted excerpts during block 415. The method 400 then proceeds to block 420.

At block 420, the Cognitive Interpretation Application 105 determines whether the selected document (or the portion that was analyzed) includes any comparative statements. If so, the method 400 continues to block 425. If not, the method 400 proceeds to block 430. At block 425, the Cognitive Interpretation Application 105 generates one or more RESs 140 for each of the identified comparative statements found. The method 400 then continues to block 430. At block 430, the Cognitive Interpretation Application 105 determines whether there is at least one additional document in the corpus that is yet to be processed. If so, the method 400 returns to block 410. Otherwise, the method 400 continues to block 435, where the Knowledge Graph Component 110 generates (or updates) a knowledge graph.

Figure 5:
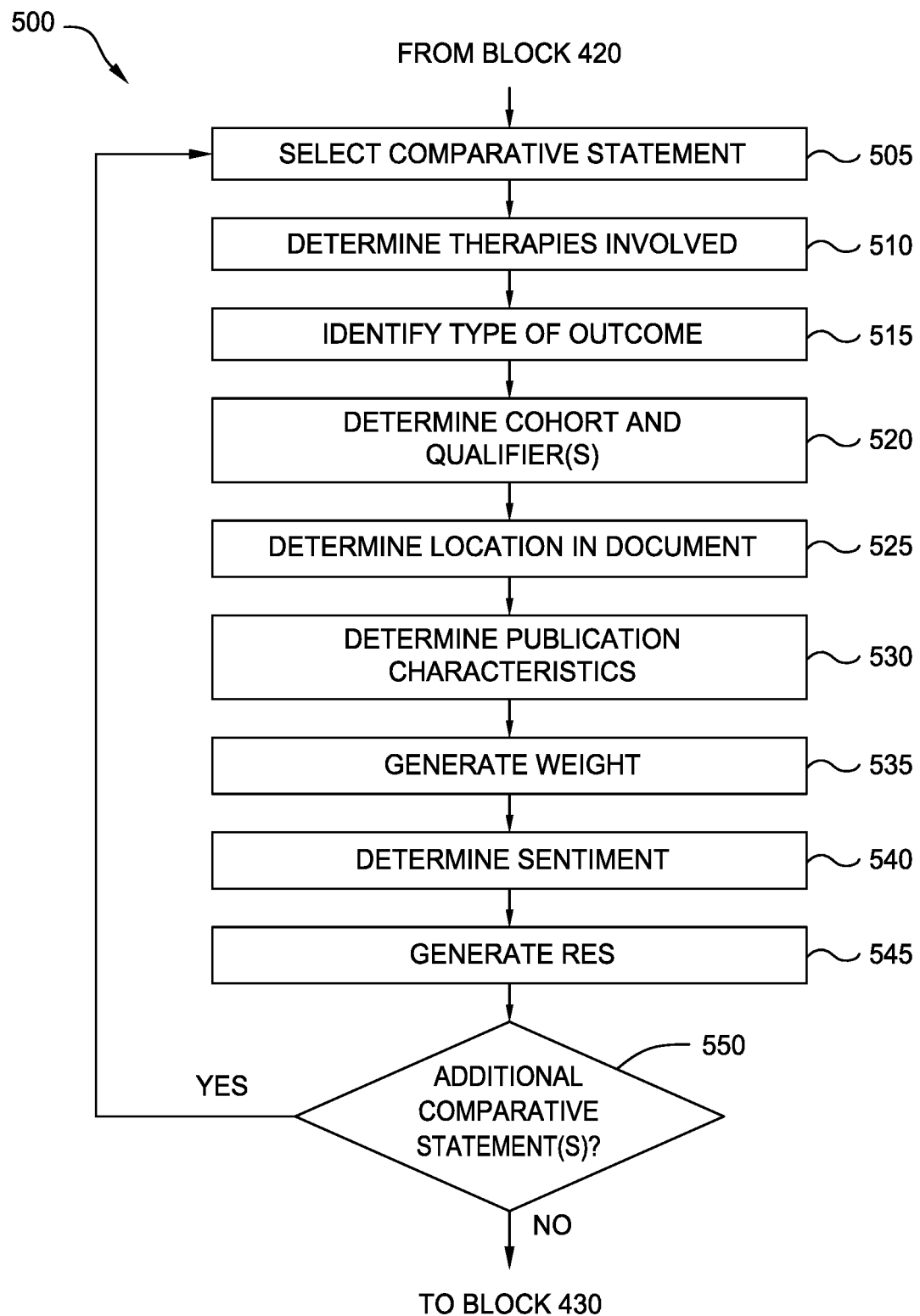
FIG. 5 is a flow diagram illustrating a method for generating relative efficacy structures summarizing comparisons between therapies, according to one embodiment disclosed herein.

FIG. 5 is a flow diagram illustrating a method 500 for generating RESs 140 summarizing comparisons between therapies, according to one embodiment disclosed herein. In one embodiment, the method 500 provides additional detail for block 425 in FIG. 4. The method 500 begins at block 505, where the Cognitive Interpretation Application 105 selects one of the comparative statements that were identified in the selected document. At block 510, the Cognitive Interpretation Application 105 identifies the therapies that are implicated by the selected statement. In one embodiment, the Cognitive Interpretation Application 105 utilizes NLP techniques to identify the relevant therapies. As discussed above, in some embodiments, the Cognitive Interpretation Application 105 parses other sections of the document, and/or other documents and data, in order to disambiguate any unknown or uncertain terms (e.g., ambiguous phrases or acronyms). The method 500 then continues to block 515.

At block 515, the Cognitive Interpretation Application 105 identifies the type of outcome the statement is addressing. That is, the Cognitive Interpretation Application 105 determines the particular outcome or effect that the selected statement is referring to. For example, in a medical embodiment, the outcomes can include overall survival, progression-free survival, remission, cure, death, complications, side effects, and the like. The method 500 then continues to block 520, where the Cognitive Interpretation Application 105 determines the cohort and/or cohort qualifiers that are relevant to the statement. For example, the cohort may be determined based on the patients being studied (e.g., as indicated by criteria used by the study authors when enrolling patients), and the cohort qualifiers can include any additional limitations included in the statement (e.g., "only patients above 65 saw a significant improvement.").

At block 525, the Cognitive Interpretation Application 105 determines the location in the selected document where the selected comparative statement was found. In one embodiment, block 525 comprises determining the section that the statement was in. In an embodiment, the sections are identified based on defined headings, metadata tags, and the like. In some embodiments, the weight of the generated RES 140 is adjusted based on the location. That is, in one embodiment, each section is associated with a respective weight or scale. For example, in one embodiment, the conclusion and abstract sections may be afforded higher weight than the general discussion section.

The method 500 then continues to block 530, where the Cognitive Interpretation Application 105 determines publication characteristics of the selected document that the statement was found in. For example, in one embodiment, the publication characteristics include a date when the document was published, the identity of the publisher, whether it has been peer-reviewed, and the like. In some embodiments, the publication characteristics also include the location in the document where the comparative statement was found. At block 535, the Cognitive Interpretation Application 105 generates a weight for the RES 140 based on the publication characteristics, and/or the determined location. In some embodiments, the Cognitive Interpretation Application 105 also considers any confidence values generated by the NLP models when parsing the text. Further, in one embodiment, the weight is based in part on the strength of the comparator used (e.g., whether the treatment is "slightly better" or "far superior").

The method 500 then continues to block 540, where the Cognitive Interpretation Application 105 determines the sentiment of the statement. In an embodiment, as discussed above, the Cognitive Interpretation Application 105 utilizes NLP to classify the statement as positive, negative, or neutral. Finally, at block 545, the Cognitive Interpretation Application 105 generates a RES 140 for the selected comparative statement based on the determined attributes, sentiment, and weight. At block 550, the Cognitive Interpretation Application 105 determines whether there is at least one additional comparative statement found in the document. If so, the method 500 returns to block 505. Otherwise, the method 500 terminates.

Figure 6:
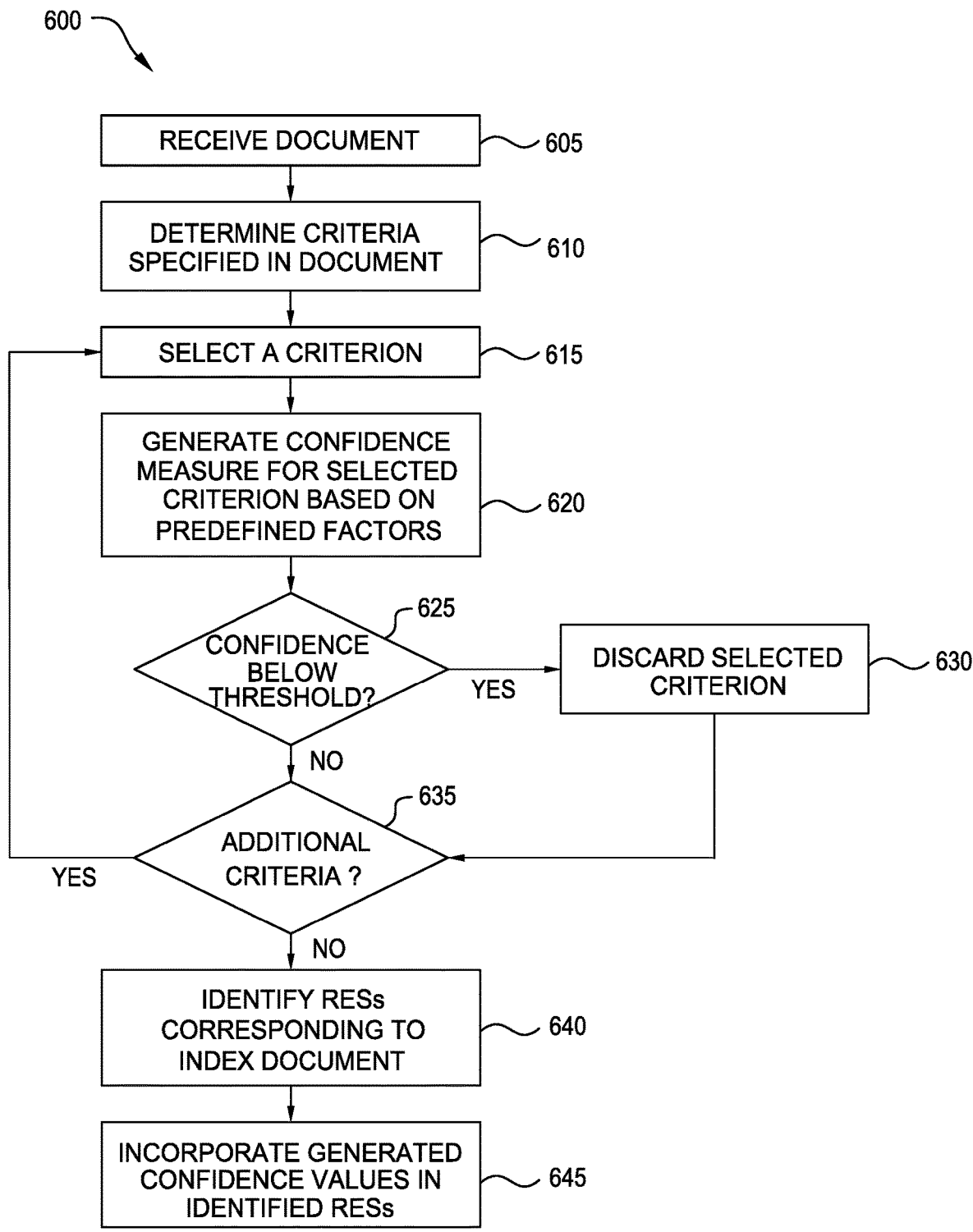
FIG. 6 is a flow diagram illustrating a method for analyzing and weighting criteria specified in documents, according to one embodiment disclosed herein.

FIG. 6 is a flow diagram illustrating a method 600 for analyzing and weighting criteria specified in documents, according to one embodiment disclosed herein. The method 600 begins at block 605, where the Criteria Weighting Component 290 receives an index document to be analyzed. In one embodiment, the method 600 is performed after the knowledge graph has been constructed, and the resulting confidence measures are incorporated into the graph. In some embodiments, the method 600 is performed alongside the method 400. For example, in one embodiment, as documents are ingested to generate RESs, they are also analyzed using the method 600 to determine a confidence measure for each stated criterion. In some embodiments, these confidence measures are then incorporated into the RES(s) corresponding to the document, and included in the knowledge graph as it is constructed.

At block 610, the Criteria Weighting Component 290 identifies the criteria that are specified by the index document. In one embodiment, the criteria are written or prepared by one or more authors of the document, and indicate the cohort of patients to which the results can be applied. In some embodiments, the criteria were used to determine patient eligibility when enrolling individuals in the study or trial (or excluding them from participation). The method 600 then proceeds to block 615, where the Criteria Weighting Component 290 selects a first of these identified criteria. At block 620, the Criteria Weighting Component 290 determines a confidence measure for the selected criterion based on one or more predefined factors. Determining a confidence measure for the selected criterion is discussed in more detail below, with reference to FIGS. 7, 8, and 9. The method 600 then proceeds to block 625.

At block 625, the Criteria Weighting Component 290 determines whether the generated confidence measure is below a predefined threshold level of confidence. If so, the method 600 proceeds to block 630, where the selected criterion is discarded. That is, if the confidence measure of the criterion is below a threshold, the criterion is not considered or included when constructing the knowledge graph. In an embodiment, if the knowledge graph has already been generated, it is modified or refined to remove the selected criterion from the index document. The method 600 then proceeds to block 635. Additionally, if, at block 625, the Criteria Weighting Component 290 determines that the confidence value for the selected criterion meets the defined minimum, the method 600 proceeds to block 635.

At block 635, the Criteria Weighting Component 290 determines whether there is at least one additional criterion specified in the index document that has not yet been analyzed. If so, the method 600 returns to block 615. Otherwise, the method 600 proceeds to block 640, where the Criteria Weighting Component 290 identifies the RES(s) that were generated based on the index document. Finally, at block 645, the Criteria Weighting Component 290 incorporates the generated confidence values into the identified RES(s). In one embodiment, if a criterion was discarded at block 630, it is not included in the RES. That is, the RES is revised to remove the discarded criterion. In some embodiments, however, the Criteria Weighting Component 290 includes the criterion with its low confidence value, or with an indication that it should not be trusted. In an embodiment, the knowledge graph can then be generated or refined based on the modified RES(s).

In some embodiments, if the confidence measure of a criterion is below the defined threshold, the criterion can be provisionally excluded, and flagged for review by a SME. In some embodiments, the entire document is flagged for such review. In such an embodiment, the SME can then review and accept the criteria, or modify it before accepting it. Upon being accepted, the criterion is incorporated into the RES and/or the knowledge graph by the Criteria Weighting Component 290. In an embodiment, as discussed above, reach RES includes an indication as to the cohort to which the comparison applies (e.g., based on the determined criteria). In one embodiment, incorporating the confidence values into the RES includes associating each specified criterion with its respective confidence value. In this way, when reviewing a particular comparison, the user can readily determine which criteria are likely to be accurate, and which may be erroneous. Further, in an embodiment, if a particular edge or link in the knowledge graph is constructed based on multiple RESs, the overall connection may similarly indicate the relevant criteria, and their respective confidence values.

In one embodiment, in order to generate scores or rankings for potential therapies for a patient, the contribution or weight of each piece of evidence (e.g., each statement or comparison in the knowledge graph) is based on how closely the patient's attributes align with the criteria associated with the statement. In some embodiments, the criteria are evaluated to generate an overall match or fitness score indicating the variance between the user's attributes and the stated criteria. In one embodiment, to generate the overall fitness score, the criteria are weighted based on their confidence values. Thus, in an embodiment, a criterion associated with higher confidence is given higher weight in assigning a match score. Further, in an embodiment, the match score is based in part on the magnitude of the difference between the criteria and the patient's attributes. In this way, the evidence can be weighted based on the fitness or match score, which was generated based on the weighted magnitude between the criterion and the actual patient attribute (based on the confidence values associated with each criterion).

Figure 7:
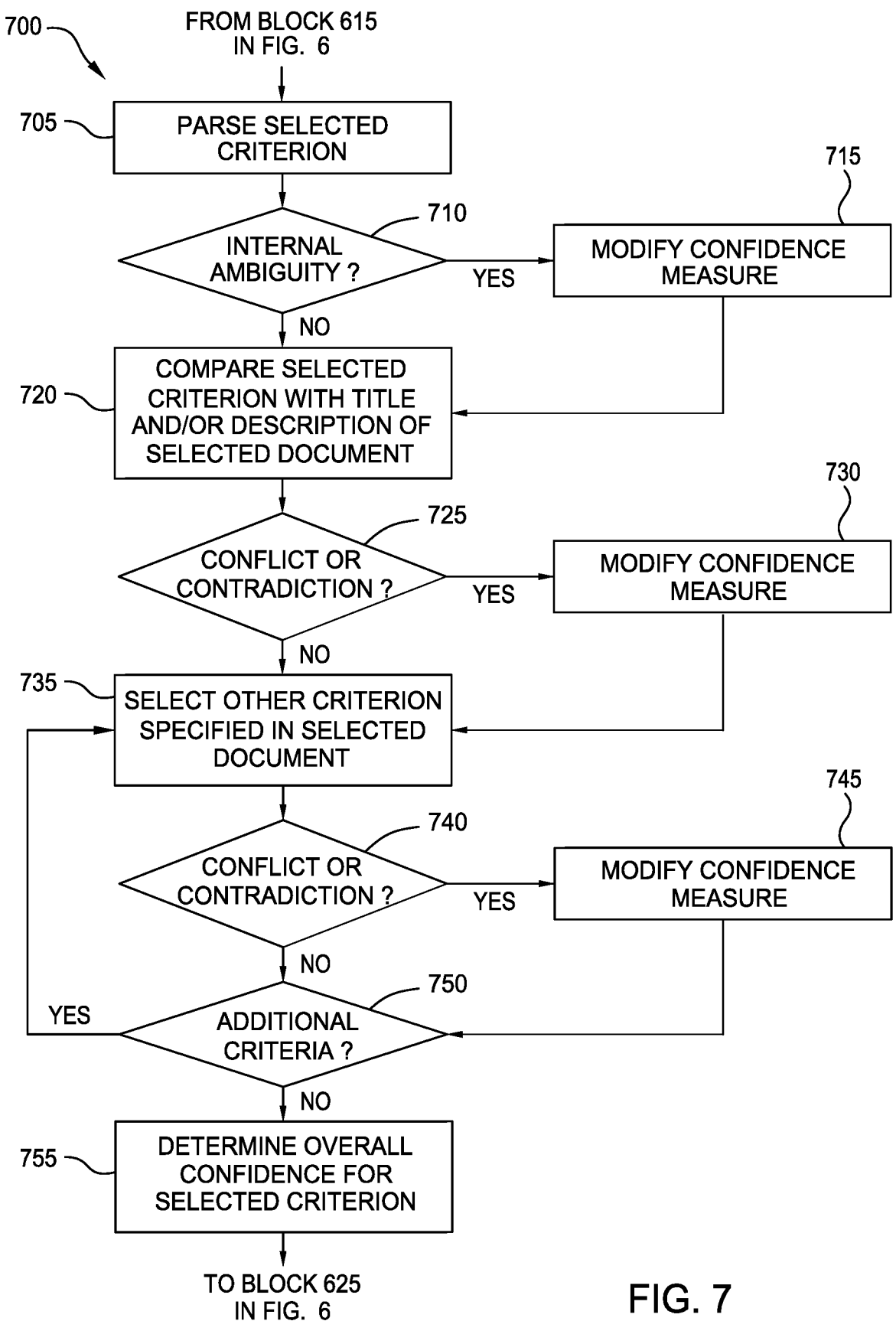
FIG. 7 is a flow diagram illustrating a method for evaluating criteria based on logical parsing, according to one embodiment disclosed herein.

FIG. 7 is a flow diagram illustrating a method 700 for evaluating criteria based on logical parsing, according to one embodiment disclosed herein. In an embodiment, the method 700 provides additional detail for block 620 in FIG. 6. The method 700 begins at block 705, where the Criteria Weighting Component 290 parses the selected criterion using one or more NLP techniques. In one embodiment, the NLP techniques include predefined word or phrase patterns to identify potential ambiguity or contradiction. For example, one such pattern may be used to determine whether the criterion states that the study applies to patients who have "A or B and C," "A or B or C," and the like, where A, B, and C are attributes of the patient. In some embodiments, the predefined patterns can also include an indication as to punctuation that can indicate potential problems. For example, one such pattern can indicate that the absence of an Oxford comma may cause ambiguity, or that the presence of a semi-colon is associated with increased likelihood of confusion or ambiguity (e.g., because the criterion may actually include multiple attributes, or may be contradictory).

In some embodiments, the NLP techniques include parsing the criterion to determine the meaning of it, and whether it is internally consistent. For example, in one embodiment, the Criteria Weighting Component 290 utilizes an ontology that identifies relationships between phrases, words, or concepts, as well as the meaning for each concept. In one embodiment, if the Criteria Weighting Component 290 determines that the meaning of the criterion is unclear (e.g., because it cannot be parsed in an understandable manner), the confidence value of the criterion is reduced. Further, in an embodiment, the Criteria Weighting Component 290 determines whether the criterion contradicts itself, and adjusts the confidence accordingly. For example, if the selected criterion states that the study applies to patients with "stage four non-metastatic cancer," the Criteria Weighting Component 290 can determine, based on the ontology, that the concepts or attributes of "stage four cancer" and "non-metastatic cancer" are mutually exclusive, and thus that all or a portion of the criterion is likely incorrect or erroneous.

In one embodiment, the NLP techniques include parsing the criterion to determine whether it is open-ended or flexible. In one embodiment, this is based on defined words that indicate flexibility or uncertainty. For example, if the criterion states that the study should include patients with a "reasonable" BMI, the Criteria Weighting Component 290 can determine that this criterion is ambiguous. Similarly, if the criterion relies on or refers to the professional judgment of an SME, the Criteria Weighting Component 290 can determine that its confidence should be reduced. Additionally, in one embodiment, if the criterion includes open-ended language such as "or other attributes deemed suitable," or "and other similar illnesses," the Criteria Weighting Component 290 can determine that the selected criterion is unclear.

In some embodiments, in addition to utilizing predefined patterns and NLP techniques, the Criteria Weighting Component 290 utilizes one or more machine learning (ML) models to identify ambiguity and/or to assign confidence values. For example, in one embodiment, a ML model can be trained using labeled exemplars. That is, a criterion can be provided as input, with an indication as to whether the criterion is ambiguous (or a defined confidence value) used as the target output. The ML model can then be refined (e.g., one or more internal weights can be adjusted) to iteratively train the model using training data. Once trained, in an embodiment, the Criteria Weighting Component 290 can process new criterion using the trained model in order to determine whether there is internal ambiguity (or in order to determine a confidence value based on internal ambiguity).

Once the Criteria Weighting Component 290 has parsed the selected criterion using one or more NLP techniques, the method 700 proceeds to block 710, where the Criteria Weighting Component 290 determines whether any internal ambiguity or inconsistency has been detected. That is, the Criteria Weighting Component 290 determines whether the selected criterion matches any of the predefined patterns for ambiguity, or whether the criterion is inconsistent, ambiguous, or contradictory based on the ontology and/or one or more ML models. If so, the method 700 proceeds to block 715, where the Criteria Weighting Component 290 modifies the confidence measure associated with the criterion (such as by reducing it). In one embodiment, each criterion is associated with an initial confidence value, and the value is reduced when potential ambiguities are identified. In some embodiments, the confidence value can be increased if no potential ambiguities are found.

In one embodiment, the confidence measure for the selected criterion is modified at block 715 based in part on the number of potential issues identified. For example, if the criterion's language aligns with two predefined patterns of potential ambiguity, the Criteria Weighting Component 290 can reduce the confidence measure by more than if the criterion satisfied one pattern. In some embodiments, each pattern is associated with a score or indication as to how much the confidence value of the criterion should be reduced if the pattern is met. Similarly, in an embodiment, each type of ambiguity identified by parsing the criterion using NLP techniques including the use of an ontology and/or ML models (e.g., direct contradiction, potential conflict, open-ended statements, and the like) is associated with a predefined indication as to how much the respective ambiguity should affect the confidence measure.

Returning to block 710, if the Criteria Weighting Component 290 determines that the selected criterion does not include internal ambiguity, the method 700 proceeds to block 720, where the Criteria Weighting Component 290 compares the selected criterion with the title of the relevant document, and/or the description or other portions of the document. That is, in the illustrated embodiment, the Criteria Weighting Component 290 identifies and extracts the title of the received or selected document from which the criterion was extracted, the abstract of the document, the description section, or any other section of the document (or the entire document). The Criteria Weighting Component 290 then uses one or more NLP techniques, such as by utilizing the ontology discussed above, to determine whether the criterion appears to conflict or contradict the remaining text in the document. For example, suppose the criterion indicates that the study is open to participants who are "younger than 25," but the title of the study is "Efficacy of therapy X in teenaged patients." In an embodiment, based on an ontology, the Criteria Weighting Component 290 can determine that the criterion therefore conflicts with the stated purpose of the trial.

As another example, suppose that the criterion indicates that the study applies to patients with any type of cancer, but that the abstract of the document indicates that purpose of the study is to determine the efficacy of a therapy for patients with metastatic cancer. In such an embodiment, even though the criterion does not directly contradict or conflict with the text, the Criteria Weighting Component 290 can nevertheless reduce confidence of the criterion, based on determining that it may be broader or more inclusive than the study author intended. Similarly, in an embodiment, if the criterion appears narrower than intended, the Criteria Weighting Component 290 can reduce the corresponding confidence value. In embodiments, the Criteria Weighting Component 290 can analyze the text of any section of the document in order to determine whether the criterion aligns with the rest of the document. In some embodiments, the user can specify which section(s) of the document should be analyzed, the weight given to each section, and the like. The method 700 then proceeds to block 725.

At block 725, the Criteria Weighting Component 290 determines whether the comparison resulted in any conflict or contradiction being identified between the selected criterion and the text that was analyzed. If so, the method 700 proceeds to block 730, where the Criteria Weighting Component 290 modifies the confidence measure of the selected criterion (e.g., by reducing it). In an embodiment, as discussed above, the magnitude of the modification can be based in part on the number of inconsistencies identified, the significance of the inconsistencies, the section(s) of the document where the inconsistency was found, and the like. The method 700 then proceeds to block 735.

Returning to block 725, if the Criteria Weighting Component 290 determines that the criterion is consistent with the text of the document, the method 700 continues to block 735. Although not illustrated, in some embodiments, the Criteria Weighting Component 290 similarly increases the confidence measure if it is determined that the criterion is consistent with the surrounding text. At block 735, the Criteria Weighting Component 290 selects one of the other criteria included in the selected or received document. The method 700 then proceeds to block 740, where the Criteria Weighting Component 290 determines whether the first criterion (e.g., the criterion selected in block 615 of FIG. 6) conflicts or contradicts with the second criterion (e.g., the criterion selected in block 735).

In one embodiment, the Criteria Weighting Component 290 makes this determination by using one or more NLP techniques, as discussed above. For example, in an embodiment, the Criteria Weighting Component 290 parses each of the selected criteria, and compares the resulting evaluations (e.g., using one or more ontologies) to determine whether they contradict each other. If so, the method 700 proceeds to block 745, where the Criteria Weighting Component 290 modifies the confidence measure of the selected criterion (e.g., by reducing it), as discussed above. If not, the method 700 proceeds to block 750. At block 750, the Criteria Weighting Component 290 determines whether there is at least one additional other criterion to which the initially selected criterion should be compared. If so, the method 700 returns to block 735. Otherwise, the method 700 continues to block 755.

At block 755, the Criteria Weighting Component 290 determines an overall confidence value for the selected criterion, based on the above evaluations. That is, in the illustrated embodiment, the Criteria Weighting Component 290 generates a final confidence value that is based on aggregating the internal ambiguities and inconsistencies, conflicts between the criterion and all or a portion of the corresponding document, and contradictions between the criterion and the other criteria specified by the document. In this way, the Criteria Weighting Component 290 can determine an overall confidence value with respect to the document itself (e.g., in the context of the particular study or trial).

Figure 8:
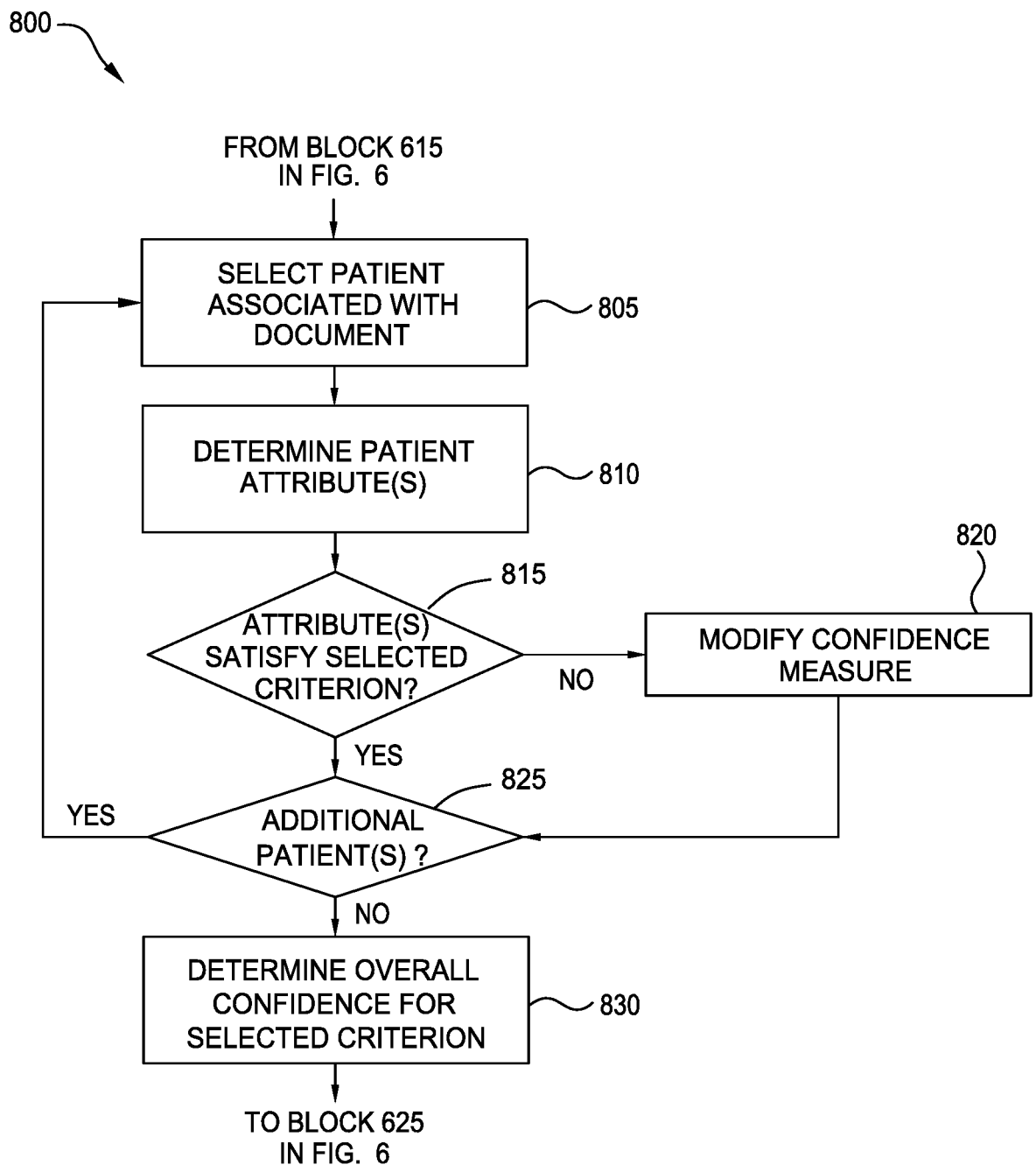
FIG. 8 is a flow diagram illustrating a method for evaluating criteria based on participant attributes, according to one embodiment disclosed herein.

FIG. 8 is a flow diagram illustrating a method 800 for evaluating criteria based on participant attributes, according to one embodiment disclosed herein. In an embodiment, the method 800 provides additional detail for block 620 in FIG. 6. The method 800 begins at block 805, where the Criteria Weighting Component 290 selects one of the patients or participants associated with the received or selected document. As discussed above, in an embodiment, the document corresponds to a clinical trial or study that enrolled patients to participate in the study (e.g., to receive medication or other therapy being tested) in order to determine the efficacy of a therapy, potential side effects, and the like. In an embodiment, at block 805, the Criteria Weighting Component 290 selects one of those patients who participated in the study. The method 800 then proceeds to block 810.

At block 810, the Criteria Weighting Component 290 determines the attributes of the selected participant, if available. In an embodiment, one or more attributes of one or more of the participants may be available in the document itself (or in an appendix or supplement to the document). In one embodiment, this data is available elsewhere (e.g., in one or more other data stores). In some embodiments, the attributes are anonymized (e.g., such that the Criteria Weighting Component 290 can analyze the attributes, but cannot specifically identify any particular individual to whom the attributes belong. At block 815, the Criteria Weighting Component 290 determines whether the determined attributes satisfy the selected criterion. That is, the Criteria Weighting Component 290 determines whether the selected participant aligns with the selected criterion. If not, the method 800 proceeds to block 820, where the Criteria Weighting Component 290 modifies the confidence measure of the selected criterion. That is, because the selected patient was enrolled in the study or trial despite failing to meet the required criterion, the Criteria Weighting Component 290 determines that the criterion may be erroneous or misleading, or was not relied on when enrolling patients, and thus reduces the confidence level. The method 800 then proceeds to block 825.

Returning to block 815, if the Criteria Weighting Component 290 determines that the selected participant satisfies the criterion, the method 800 continues to block 825. At block 825, if the Criteria Weighting Component 290 determines whether there is at least one additional participant in the study that has not yet been analyzed. If so, the method 800 returns to block 805. Otherwise, the method 800 proceeds to block 830, where the Criteria Weighting Component 290 determines an overall confidence for the selected criterion. In one embodiment, this confidence value is based in part on the number or percentage of participants or patients who did not satisfy the criterion, but were nevertheless enrolled in the trial. In some embodiments, the confidence value is further based on how much each participant differed from the criterion (e.g., how close the patients were to satisfying the criterion). For example, in such an embodiment, if the criterion requires that patients weigh more than 100 pounds and one patient weighed 98 pounds, the Criteria Weighting Component 290 may assign a relatively higher confidence value than if the patient weighed 50 pounds.

Thus, in the illustrated embodiment, the Criteria Weighting Component 290 generates a confidence value for the selected criterion based on how closely the actual study participants align with the criterion. In one embodiment, the Criteria Weighting Component 290 can generate distinct confidence scores, where a first is based on the text of the document (e.g., using the method 700), and a second considers the actual patients involved. In some embodiments, these scores are aggregated to generate a single overall score. In one embodiment, when aggregating the scores generated based on each class of evidence, the Criteria Weighting Component 290 can weight each individual score based on user preferences (e.g., based on whether the user prefers to rely on the actual text of the document, the actual participants, or a combination of both).

Figure 9:
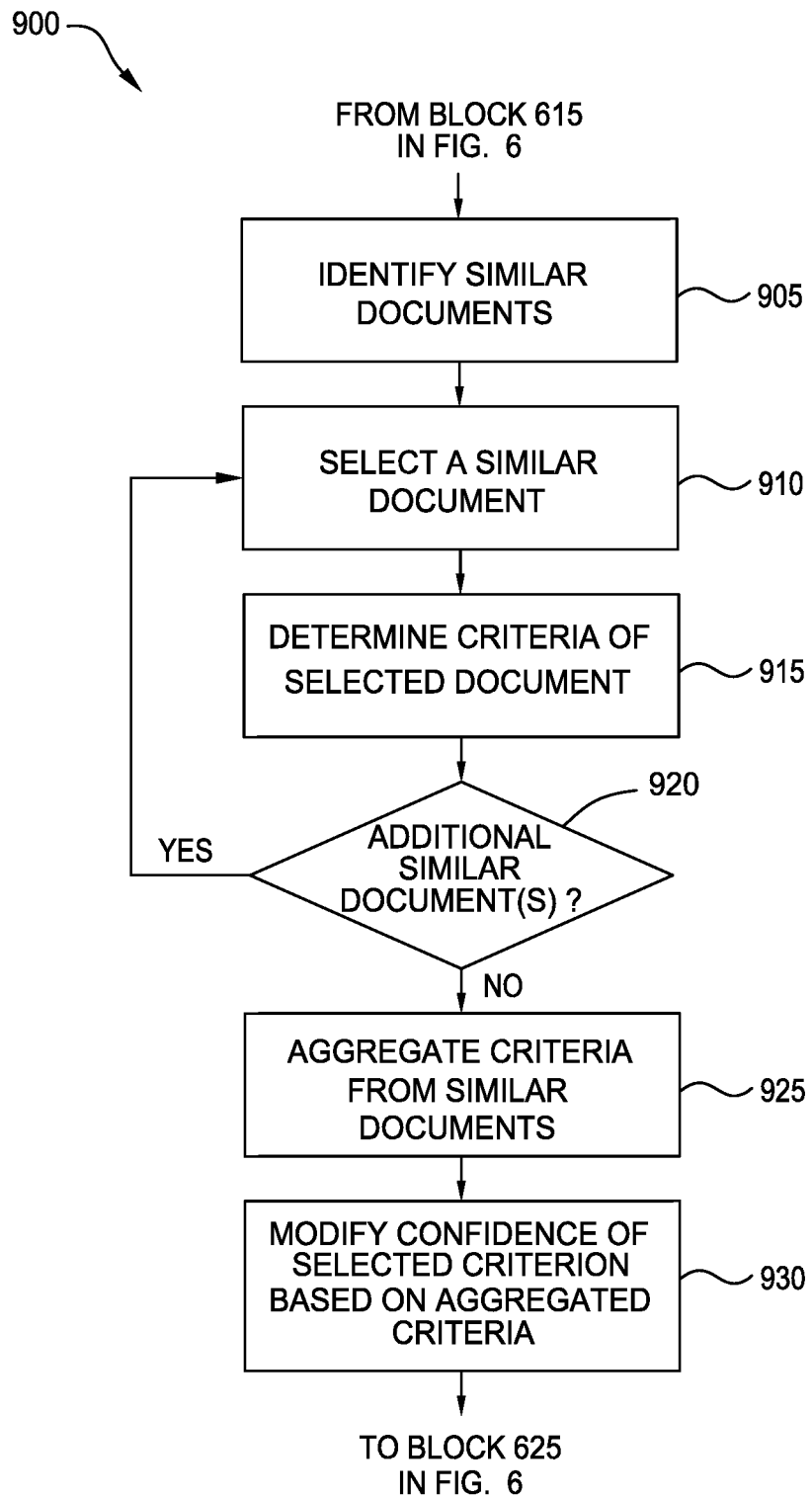
FIG. 9 is a flow diagram illustrating a method for evaluating criteria based on published literature, according to one embodiment disclosed herein.

FIG. 9 is a flow diagram illustrating a method 900 for evaluating criteria based on published literature, according to one embodiment disclosed herein. In an embodiment, the method 800 provides additional detail for block 620 in FIG. 6. In some embodiments, the method 800 can be combined with the method 700 and/or 800, in order to generate or refine the confidence values based on additional sources of evidence. The method 900 begins at block 905, where the Criteria Weighting Component 290 identifies one or more other documents (e.g., from the Corpus 115) that are similar or related to the received or selected document. In one embodiment, the Criteria Weighting Component 290 identifies similar documents based on a variety of factors, including the disorder(s) being studied, the therapy or therapies being evaluated, the amount that the criteria specified by each document overlap, and the like. In some embodiments, the Criteria Weighting Component 290 generates a similarity score for each of the one or more other documents based on these factors, and evaluates documents with a score exceeding a predefined threshold.

The method 900 then proceeds to block 910, where the Criteria Weighting Component 290 selects one of the identified similar documents. At block 915, the Criteria Weighting Component 290 determines (e.g., identifies and extracts) the criteria specified in the selected similar document. The method 900 then proceeds to block 920, where the Criteria Weighting Component 290 determines whether there is at least one additional similar document to be considered. If so, the method 900 returns to block 910. Otherwise, the method 900 proceeds to block 925, where the Criteria Weighting Component 290 aggregates the criteria extracted from the similar documents. In one embodiment, aggregating the criteria includes determining, for each of the criteria, a number or percentage of the similar documents that included the respective criterion. The method 900 then proceeds to block 930.

At block 930, the Criteria Weighting Component 290 modifies the confidence value of the selected criterion based on the aggregated criteria from similar documents. In one embodiment, the Criteria Weighting Component 290 can determine a percentage of number of the aggregated criteria that the selected criterion aligns with, and generate or modify the confidence of the selected criterion. For example, in such an embodiment, if the selected criterion is also found in 75% of the similar documents, it will receive a relatively higher confidence value than if the selected criterion was only found in 10% of the similar documents.

In one embodiment, in addition to determining whether the selected criterion is found in the aggregated criteria, the Criteria Weighting Component 290 also considers whether the selected criterion is more specific or exclusive. For example, if the selected criterion requires that participants be at least 75 years of age, the Criteria Weighting Component 290 may determine that this criterion aligns with aggregated criteria requiring the patients be 75 or older, but also with criteria requiring that participants be at least 65. Generally, at block 930, the Criteria Weighting Component 290 increases or reduces the confidence value of the selected criterion based on how closely the selected criterion aligns with the aggregate criteria given by related or similar documents.

Although not depicted in the illustrated embodiment, in some embodiments, the Criteria Weighting Component 290 can also suggest new criteria based on a variety of factors. For example, in one embodiment, if the text or abstract of the document indicates that a particular attribute is relevant to the study, but no criteria corresponds to this attribute, the Criteria Weighting Component 290 can generate a new criterion reflecting this attribute. Similarly, if all of the participants in the selected document (or a percentage exceeding a predefined threshold) have a particular attribute or satisfy a particular criterion that is not explicitly specified, the Criteria Weighting Component 290 may determine that this criterion should be included with a relatively high level of confidence. In this way, the Criteria Weighting Component 290 can not only exclude criteria that are likely erroneous, but also include criteria that were likely omitted by mistake.

Figure 10:
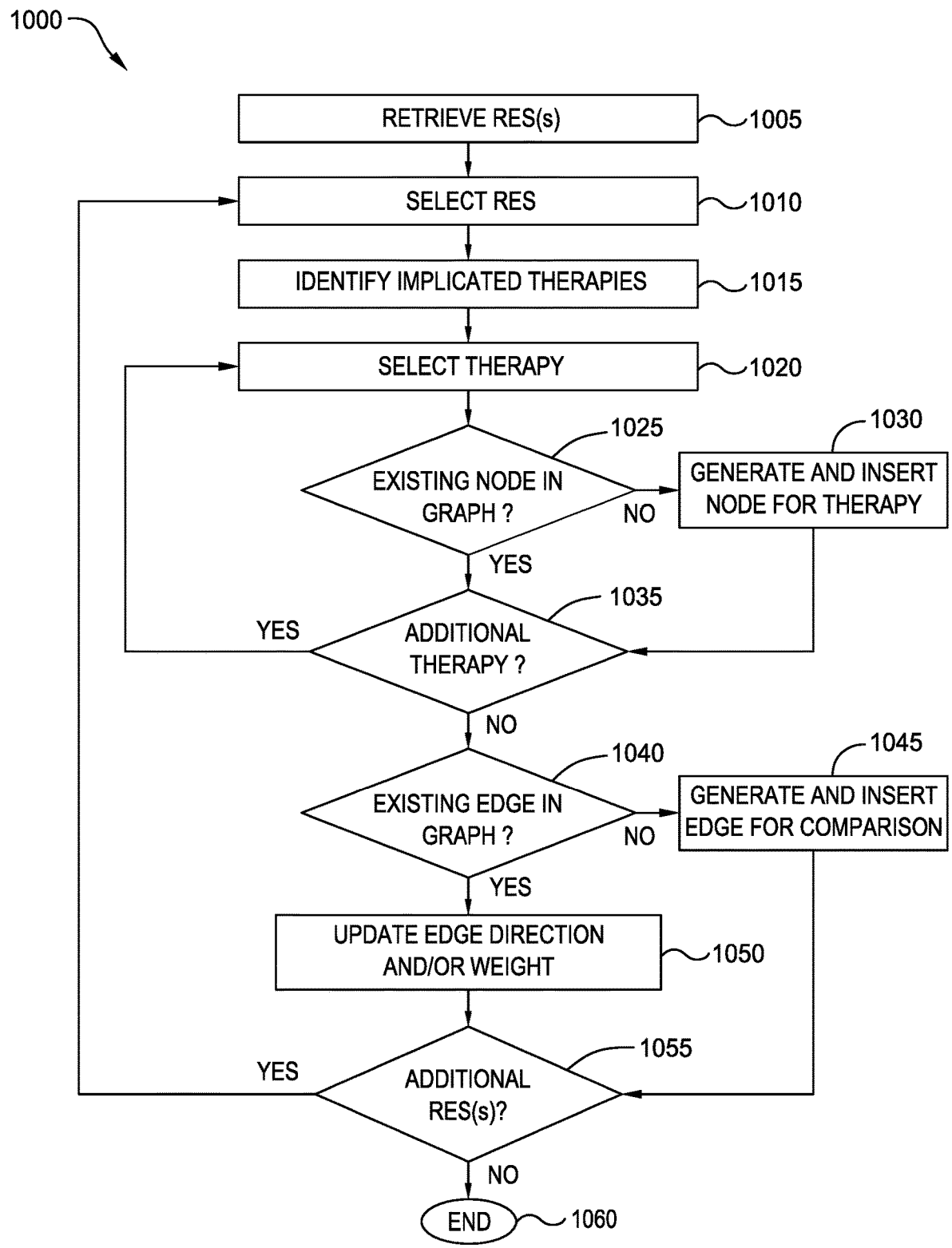
FIG. 10 is a flow diagram illustrating a method for generating a knowledge graph based on generated relative efficacy structures, according to one embodiment disclosed herein.

FIG. 10 is a flow diagram illustrating a method 1000 for generating a knowledge graph based on generated relative efficacy structures, according to one embodiment disclosed herein. The method 1000 begins at block 1005, where the Knowledge Graph Component 110 retrieves one or more RES(s) 140 that were generated by the Cognitive Interpretation Application 105. At block 1010, the Knowledge Graph Component 110 selects one of the RESs 140. The method 1000 then proceeds to block 1015, where the Knowledge Graph Component 110 identifies the therapies that are indicated by the selected RES 140. That is, the Knowledge Graph Component 110 determines which therapies are compared in the RES 140. At block 1020, the Knowledge Graph Component 110 selects one of these identified therapies.

The method 1000 continues to block 1025, where the Knowledge Graph Component 110 determines whether there is an existing node in the knowledge graph for the selected therapy. As discussed above, in an embodiment, each node in the knowledge graph corresponds to a therapy. In some embodiments, a therapy can include a combination of treatments or mediations (e.g., a drug as well as physical therapy). If the selected therapy is already represented in the knowledge graph, the method 1000 continues to block 1035. If the selected therapy is not yet in the knowledge graph, the method 1000 proceeds to block 1030, where the Knowledge Graph Component 110 generates and inserts a new node into the graph to represent the selected therapy. The method 1000 then continues to block 1035.

At block 1035, the Knowledge Graph Component 110 determines whether there are additional therapies in the selected RES 140. If so, the method 1000 returns to block 1020. Otherwise, the method 1000 continues to block 1040. In the illustrated embodiment, the Knowledge Graph Component 110 analyzes each therapy, and generates new nodes for each. In some embodiments, the knowledge graph is already constructed using a known or defined set of therapies. In such an embodiment, the Knowledge Graph Component 110 does not generate and insert new nodes. In some embodiments, in addition to an existing set of therapies, the Knowledge Graph Component 110 can further generate and insert nodes representing new therapies or new combinations of treatments that are identified in the RES 140.

In one embodiment, each node in the knowledge graph can be connected to zero or more other nodes, based on whether a comparison has been identified between the corresponding therapies. For example, in one embodiment, if two therapies have not been directly compared in the published literature, there will be no link or connection between the corresponding nodes. If, however, the therapies have been compared at least once, there will be an edge or connection between them. In some embodiments, each edge includes a number of dimensions indicating the directionality, the cohort(s) the edge applies to, the outcome(s) the edge applies to, and the like. For example, in such an embodiment, an edge may indicate that treatment A is better than treatment B, with respect to overall survival, in patients over 65. For patients under 65, however, there may be no edge or connection (if the therapies have not been compared for patients under 65), or there may be a link indicating that treatment B is better than treatment A. Similarly, with respect to a different outcome (such as progression-free survival or side effects), there may be no link, or a different link or connection may indicate that treatment B is better than treatment A. In some embodiments, the knowledge graph is constructed with a single edge connecting each pair of therapies, where that edge identifies all documents and/or RESs 140 that included a statement comparing the respective therapies. In another embodiment, the graph can include a respective edge to represent each respective RES 140 that is relevant to the respective pair of therapies.

In some embodiments, each edge in the graph is associated with a respective weight. This weight can be based on a variety of factors, including the number of times the relationship has been identified (e.g., the number of RESs 140 associated with the particular edge), the confidence or weight of each of those RESs 140, and the like. In some embodiments, as additional RESs 140 indicate the same relative efficacy (e.g., that one therapy is better than the other), the weight or strength of the edge is progressively strengthened. If, however, a RES 140 indicates the opposite comparison (e.g., that the first therapy is worse than the other), the weight or strength of the edge is reduced. In this way, each connection in the graph indicates an overall relative efficacy of the therapies, along with an associated strength or confidence in the accuracy of the comparison.

At block 1040, the Knowledge Graph Component 110 determines whether there is an existing edge in the knowledge graph representing the relationship indicated by the selected RES 140. That is, in an embodiment, the Knowledge Graph Component 110 determines whether there is any link or connection between the identified therapies, with respect to the indicated cohort and outcome, regardless of the directionality of the relationship (e.g., regardless of whether the existing link matches the determined relative efficacy in the RES 140). In an embodiment, there may be any number of connections between the identified therapies with respect to other cohorts or other outcomes. The determination at block 1040, however, is specific to the particular cohort and outcome specified in the RES 140.

In some embodiments, a particular RES 140 can include multiple comparisons. For example, if a statement included that treatment A was superior than all known treatments, the Cognitive Interpretation Application 105 can parse or analyze existing literature (or one or more knowledge graphs) to identify known treatments with respect to the disorder, cohort, and outcome. In such an embodiment, the RES 140 can include an indication of each of these known treatments. In other embodiments, a separate RES 140 is created for each of the comparisons (e.g., for each of the known treatments). In an embodiment, if the RES 140 includes comparisons to multiple therapies, the process discussed below (and reflected by blocks 1040, 1045, and 1050) is repeated for each.

If the Knowledge Graph Component 110 determines, at block 1040, that there is no edge in the graph representing the comparison, with respect to the identified cohort and outcome, the method 1000 continues to block 1045, where the Knowledge Graph Component 110 generates and inserts one. In one embodiment, the directionality of the new edge is based on the sentiment reflected in the selected RES 140 (e.g., positive, negative, or neutral). Further, in an embodiment, the initial weight or strength of the new edge is based on the weight or confidence of the RES 140. Further, in one embodiment, the weight or confidence of the edge is based in part on the confidence values related to each particular criterion associated with the RES 140. In some embodiments, the edge is associated with the determined confidence values, such that when the graph is evaluated with respect to a particular patient, the weight of the edge can be modified based on the patient's attributes and the criteria confidences. In this way, the knowledge graph is updated to reflect that the published literature includes a direct comparison between the therapies, and indicates the relative efficacy of the therapies (e.g., based on the directionality of the edge).

If the Knowledge Graph Component 110 determines, at block 1040, that an edge already exists for the indicated comparison, with respect to the specified cohort and outcome, the method 1000 continues to block 1050, where the Knowledge Graph Component 110 updates the weight and/or direction of the identified edge. In some embodiments, the Knowledge Graph Component 110 instead inserts a new edge, depending on the particular design that will be used to represent multiple comparisons between two treatments in the knowledge graph. As discussed above, in one embodiment, this updating includes adjusting the weight of the edge based on the weight and directionality of the selected RES 140. In an embodiment, if the sentiment reflected by the RES 140 is in the same direction as the existing edge (e.g., the RES 140 and the edge agree that one treatment is superior), the weight or strength is increased. If the directions are opposite, the weight is decreased. Similarly, in one embodiment, if the selected RES 140 has a neutral sentiment (indicating that the therapies are equally effective), the weight of the edge is reduced, regardless of which direction it currently points. If the edge is already neutral, a neutral weight or strength can be increased, indicating that there is additional evidence that the therapies are equally effective.

In one embodiment, the amount that the edge strength is changed is dependent on the magnitude of the confidence or weight associated with the RES 140. If the RES 140 is associated with a high weight, the strength of the edge will be adjusted a greater amount than if the weight of the RES 140 was low. In one embodiment, if the weight falls below a predefined threshold (e.g., within a defined distance from zero), the edge is removed from the graph, indicating that there is no medical consensus regarding the relationship or relative efficacy. In other embodiments, the edge is updated to have no direction, reflecting that there is no solid consensus, and results are mixed (e.g., indicating that the comparison has been studied, but that there is no strong evidence supporting either therapy as more effective than the other). In some embodiments, this edge is retained with a low weight or strength, and is assigned a neutral sentiment to indicate that neither therapy is clearly superior to the other.

Similarly, in some embodiments, if an edge is neutral (or close to neutral) and the weight adjustment would cause the weight to be negative, the direction of the edge is switched, indicating a (potentially weak) new consensus that the relative efficacy of the treatments is reversed from the previously-understood comparison. In some embodiments, each edge in the graph is associated with a directionality as well as a weight or strength of the edge (representing the strength of the evidence). The method 1000 then proceeds to block 1055, where the Knowledge Graph Component 110 determines whether there is at least one additional RES 140 that has not been analyzed and ingested into the knowledge graph. If so, the method 1000 returns to block 1010 to select a next RES 140. Otherwise, the method 1000 terminates at block 1060. In this way, the Knowledge Graph Component 110 can update and refine the knowledge graph based on new therapies and studies. In embodiments, the knowledge graph is a multi-dimensional representation of the medical consensus as to relative efficacies of any number of therapies, with respect to any combination of particular cohorts and outcomes. Advantageously, embodiments of the present disclosure enable the graph to be continuously and rapidly updated when new published literature becomes available, such that the knowledge graph represents the most up-to-date and accurate representation possible. Further, because of the high-dimensionality of the graph (e.g., because the relative efficacies differ based on the individual cohort and outcome), the knowledge graph provides additional data that is far more granular, and is not otherwise available to healthcare providers.

In some embodiments, the knowledge graph can be accessed and searched by healthcare providers in order to determine optimal treatments for a particular patient. For example, in an embodiment, the provider can search the knowledge graph (e.g., using the User Interface 280 of the Client Device 255) to identify therapies and/or relative efficacies that are relevant to the cohort to which the patient belongs. That is, in an embodiment, the knowledge graph can be parsed to identify comparisons that are relevant to a patient in a particular cohort (e.g., having a particular set of attributes). In some embodiments, the provider can also filter, sort, or search the knowledge graph based on the desired outcome. In one embodiment, based on these relative efficacies, the therapies can be scored and ranked, in order to identify the most optimal therapy. This allows the provider to make improved decisions with respect to treating the patient.

In some embodiments, the outcomes types are associated with a predefined hierarchy. That is, some outcomes (e.g., progression-free survival) may be considered more important than other outcomes (e.g., side effects), and therefore be weighted more heavily when aggregating the relative efficacies with respect to each outcome in order to determine an overall relative efficacy (e.g., an overall optimal or best therapy, with respect to all outcomes). In such an embodiment, the ranking or scoring of the therapies may take into account the relative efficacies, as well as the importance or weight of the particular outcome. That is, although a first therapy may be the best with respect to side effects, it may be given a lower score than a second therapy that is better with respect to survival.

In an embodiment, once the knowledge graph is generated, it can be parsed or evaluated based on a particular patient, in order to identify and score relevant therapies. For example, in one embodiment, the knowledge graph is parsed to identify therapies that may be useful in treating the disorder suffered by the patient, and the patient's attributes are used to identify edges or connections that are relevant to the patient. That is, if an edge corresponds to a study that included patients under 50, the edge may be deemed relevant to the index patient if the index patient is younger than 50. In some embodiments, all edges to or from the therapy are considered relevant, and each edge is weighted based on its specified criteria. Further, in some embodiments, the weight of the edge is adjusted based on how much the index patient's attributes differ. For example, if the index patient is 55, the edge may still be considered, with a reduced weight.

In one embodiment, in addition to considering whether the index patient aligns with the criteria specified by the edge or RES, the system further considers the confidence of each of the criteria. For example, if the patient does not align with a criterion that is associated with a low confidence, the study may be assigned a relatively higher score or weight than if the criterion was associated with high confidence. In this way, when generating a score for a particular patient and therapy, the contribution of each edge in the knowledge graph (and each RES within each edge) is modified based not only on the directionality of the edge or the stated criteria, but also on the confidence that each criterion is accurate. This improves the knowledge graph and treatment systems by enabling improved scoring and therapy selection for patients.

Figure 11:
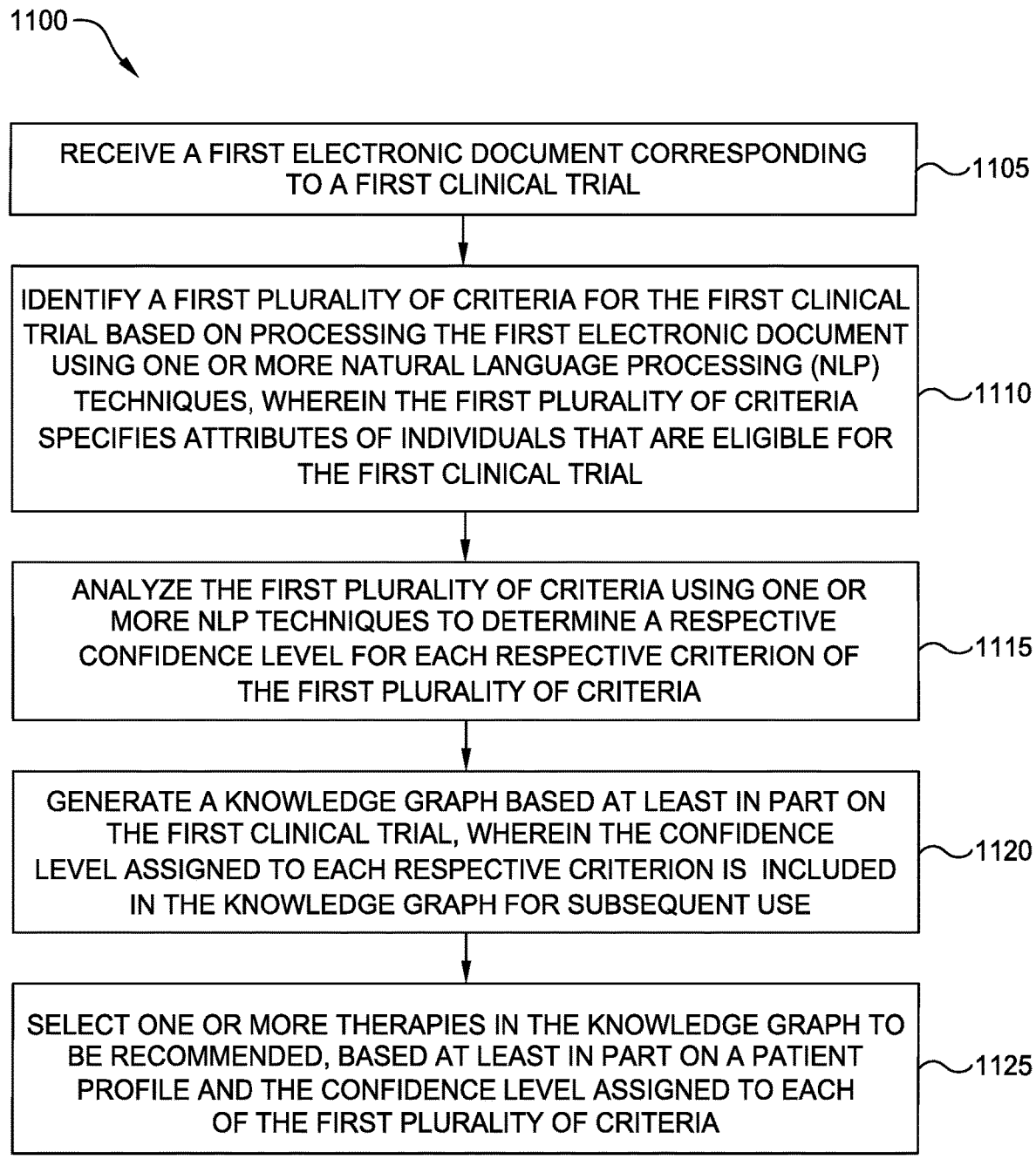
FIG. 11 is a flow diagram illustrating a method for cognitively evaluating criteria to build a knowledge graph, according to one embodiment disclosed herein.

FIG. 11 is a flow diagram illustrating a method 1100 for cognitively evaluating criteria to build a knowledge graph, according to one embodiment disclosed herein. The method 1100 begins at block 1105, where the Criteria Weighting Component 290 receives a first electronic document corresponding to a first clinical trial. The method 1100 then proceeds to block 1110, where the Criteria Weighting Component 290 identifies a first plurality of criteria for the first clinical trial based on processing the first electronic document using one or more natural language processing (NLP) techniques, wherein the first plurality of criteria specifies attributes of individuals that are eligible for the first clinical trial. Further, at block 1115, the Criteria Weighting Component 290 analyzes the first plurality of criteria using one or more NLP techniques to determine a respective confidence level for each respective criterion of the first plurality of criteria. The method 1100 then continues to block 1120, where a knowledge graph is generated based at least in part on the first clinical trial, wherein the confidence level assigned to each respective criterion is included in the knowledge graph for subsequent use. Finally, at block 1125, one or more therapies in the knowledge graph are selected to be recommended, based at least in part on a patient profile and the confidence level assigned to each of the first plurality of criteria.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the preceding features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the Criteria Weighting Component 290) or related data available in the cloud. For example, the Criteria Weighting Component 290 could execute on a computing system in the cloud and evaluate criteria for inclusion in a knowledge graph. In such a case, the Criteria Weighting Component 290 could generate confidence values for a number of criteria, and store the confidence values and criteria at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method comprising:
    receiving a first electronic document corresponding to a first clinical trial, wherein the first electronic document specifies a first plurality of criteria, wherein the first plurality of criteria specifies attributes of individuals that are eligible for the first clinical trial, and wherein the first clinical trial involved one or more therapies;
    identifying the first plurality of criteria for the first clinical trial specified in the first electronic document based on processing the first electronic document using one or more natural language processing (NLP) techniques;
    analyzing the first plurality of criteria using one or more NLP techniques to determine a respective confidence level for each respective criterion of the first plurality of criteria, wherein the respective confidence level indicates a degree of certainty that the respective criterion was required for the first clinical trial;
    determining that although the first electronic document specifies that a first criterion of the first plurality of criteria is required for participation in the first clinical trial, the first criterion was not used to select individuals for the first clinical trial based on determining that a first confidence level for the first criterion is below a first predefined threshold;
    upon determining that a confidence level for a potential new criterion exceeds a second predefined threshold, wherein the potential new criterion is not included in the first electronic document, determining that the potential new criterion was used to select individuals for the first clinical trial;
    generating, after completion of the first clinical trial, a knowledge graph based at least in part on the first clinical trial, wherein:
        the knowledge graph includes one or more nodes corresponding to the one or more therapies,
        the confidence level assigned to the potential new criterion and each respective criterion, other than the first criterion, is included in the knowledge graph for subsequent use, wherein the confidence levels are used to define weights of one or more edges in the knowledge graph,
        the potential new criterion is included in the knowledge graph, and
        the first criterion is excluded from the knowledge graph; and
    selecting one or more therapies in the knowledge graph to be recommended, based at least in part on a patient profile specifying one or more attributes for a new patient and the confidence level assigned to each of the first plurality of criteria, wherein the potential new criterion is considered, and the first criterion is not considered, when selecting the one or more therapies.

2. The method of claim 1, wherein each respective confidence level indicates a degree of certainty that the respective criterion was actually utilized when selecting individuals for the first clinical trial.

3. The method of claim 1, wherein analyzing the first plurality of criteria comprises comparing each respective criterion of the first plurality of criteria with each other criterion of the first plurality of criteria to determine a respective level of consistency.

4. The method of claim 1, wherein analyzing the first plurality of criteria comprises:
    analyzing at least one of a title or a description associated with the first clinical trial to identify a potential criterion; and
    determining whether the potential criterion conflicts with any criteria in the first plurality of criteria.

5. The method of claim 1, wherein analyzing the first plurality of criteria comprises:
    identifying at least one clinically similar trial to the first clinical trial;
    determining a second plurality of criteria for the at least one clinically similar trial; and
    comparing each criterion of the second plurality of criteria with each criterion of the first plurality of criteria to determine a respective level of consistency.

6. The method of claim 1, the method further comprising:
    upon determining that the first confidence level of the first criterion is below the predefined threshold, ignoring the first criterion when generating the knowledge graph.

7. The method of claim 1, the method further comprising:
    determining a second potential new criterion for the first clinical trial;
    determining a confidence level for the second potential new criterion; and
    upon determining that the confidence level for the second potential new criterion exceeds a predefined threshold, generating the knowledge graph based in part on the second potential new criterion.

8. The method of claim 7, wherein determining the potential criterion comprises:
    analyzing one or more attributes of at least a first individual that participated in the first clinical trial; and generating the potential criterion based on the one or more attributes of the first individual.

9. The method of claim 7, wherein determining the potential criterion comprises analyzing at least one of a title or a description associated with the first clinical trial to determine the potential criterion.

10. The method of claim 7, wherein determining the potential criterion comprises:
identifying at least one clinically similar trial to the first clinical trial; and
determining a second plurality of criteria for the at least one clinically similar trial, wherein the second plurality of criteria includes the potential criterion.

11. A computer-readable storage medium having computer-readable program code embodied therewith, the computer-readable program code executable by one or more computer processors to perform an operation comprising:
receiving a first electronic document corresponding to a first clinical trial, wherein the first electronic document specifies a first plurality of criteria, wherein the first plurality of criteria specifies attributes of individuals that are eligible for the first clinical trial, and wherein the first clinical trial involved one or more therapies;
identifying the first plurality of criteria for the first clinical trial specified in the first electronic document based on processing the first electronic document using one or more natural language processing (NLP) techniques;
analyzing the first plurality of criteria using one or more NLP techniques to determine a respective confidence level for each respective criterion of the first plurality of criteria, wherein the respective confidence level indicates a degree of certainty that the respective criterion was required for the first clinical trial;
determining that although the first electronic document specifies that a first criterion of the first plurality of criteria is required for participation in the first clinical trial, the first criterion was not used to select individuals for the first clinical trial based on determining that a first confidence level for the first criterion is below a first predefined threshold;
upon determining that a confidence level for a potential new criterion exceeds a second predefined threshold, wherein the potential new criterion is not included in the first electronic document, determining that the potential new criterion was used to select individuals for the first clinical trial;
generating, after completion of the first clinical trial, a knowledge graph based at least in part on the first clinical trial, wherein:
the knowledge graph includes one or more nodes corresponding to the one or more therapies,
the confidence level assigned to the potential new criterion and each respective criterion, other than the first criterion, is included in the knowledge graph for subsequent use, wherein the confidence levels are used to define weights of one or more edges in the knowledge graph,
the potential new criterion is included in the knowledge graph, and
the first criterion is excluded from the knowledge graph; and
selecting one or more therapies in the knowledge graph to be recommended, based at least in part on a patient profile specifying one or more attributes for a new patient and the confidence level assigned to each of the first plurality of criteria, wherein the potential new criterion is considered, and the first criterion is not considered, when selecting the one or more therapies.

12. The computer-readable storage medium of claim 11, wherein analyzing the first plurality of criteria comprises comparing each respective criterion of the first plurality of criteria with each other criterion of the first plurality of criteria to determine a respective level of consistency.

13. The computer-readable storage medium of claim 11, wherein analyzing the first plurality of criteria comprises:
analyzing at least one of a title or a description associated with the first clinical trial to identify a potential criterion; and
determining whether the potential criterion conflicts with any criteria in the first plurality of criteria.

14. The computer-readable storage medium of claim 11, wherein analyzing the first plurality of criteria comprises:
identifying at least one clinically similar trial to the first clinical trial;
determining a second plurality of criteria for the at least one clinically similar trial; and
comparing each criterion of the second plurality of criteria with each criterion of the first plurality of criteria to determine a respective level of consistency.

15. The computer-readable storage medium of claim 11, the operation further comprising:
upon determining that the first confidence level of the first criterion is below the predefined threshold, ignoring the first criterion when generating the knowledge graph.

16. A system comprising:
one or more computer processors; and
a memory containing a program which when executed by the one or more computer processors performs an operation, the operation comprising:
receiving a first electronic document corresponding to a first clinical trial, wherein the first electronic document specifies a first plurality of criteria, wherein the first plurality of criteria specifies attributes of individuals that are eligible for the first clinical trial, and wherein the first clinical trial involved one or more therapies;
identifying the first plurality of criteria for the first clinical trial specified in the first electronic document based on processing the first electronic document using one or more natural language processing (NLP) techniques;
analyzing the first plurality of criteria using one or more NLP techniques to determine a respective confidence level for each respective criterion of the first plurality of criteria, wherein the respective confidence level indicates a degree of certainty that the respective criterion was required for the first clinical trial;
determining that although the first electronic document specifies that a first criterion of the first plurality of criteria is required for participation in the first clinical trial, the first criterion was not used to select individuals for the first clinical trial based on determining that a first confidence level for the first criterion is below a first predefined threshold;
upon determining that a confidence level for a potential new criterion exceeds a second predefined threshold, wherein the potential new criterion is not included in the first electronic document, determining that the potential new criterion was used to select individuals for the first clinical trial;

generating, after completion of the first clinical trial, a knowledge graph based at least in part on the first clinical trial, wherein:
- the knowledge graph includes one or more nodes corresponding to the one or more therapies,
- the confidence level assigned to the potential new criterion and each respective criterion, other than the first criterion, is included in the knowledge graph for subsequent use, wherein the confidence levels are used to define weights of one or more edges in the knowledge graph,
- the potential new criterion is included in the knowledge graph, and
- the first criterion is excluded from the knowledge graph; and selecting one or more therapies in the knowledge graph to be recommended, based at least in part on a patient profile specifying one or more attributes for a new patient and the confidence level assigned to each of the first plurality of criteria, wherein the potential new criterion is considered, and the first criterion is not considered, when selecting the one or more therapies.

17. The system of claim 16, wherein analyzing the first plurality of criteria comprises comparing each respective criterion of the first plurality of criteria with each other criterion of the first plurality of criteria to determine a respective level of consistency.

18. The system of claim 16, wherein analyzing the first plurality of criteria comprises:
- analyzing at least one of a title or a description associated with the first clinical trial to identify a potential criterion; and
- determining whether the potential criterion conflicts with any criteria in the first plurality of criteria.

19. The system of claim 16, wherein analyzing the first plurality of criteria comprises:
- identifying at least one clinically similar trial to the first clinical trial;
- determining a second plurality of criteria for the at least one clinically similar trial; and
- comparing each criterion of the second plurality of criteria with each criterion of the first plurality of criteria to determine a respective level of consistency.

20. The system of claim 16, the operation further comprising:
- upon determining that the first confidence level of the first criterion is below the predefined threshold, ignoring the first criterion when generating the knowledge graph.

* * * * *